(12) United States Patent
Miao et al.

(10) Patent No.: US 7,351,813 B2
(45) Date of Patent: Apr. 1, 2008

(54) LIVER-SPECIFIC GENE EXPRESSION CASSETTES, AND METHODS OF USE

(75) Inventors: Carol H. Miao, Seattle, WA (US); Mark A. Kay, Los Altos Hills, CA (US)

(73) Assignees: The Board of Trustees of the Leland Stanford Junior University, Palo Alto, CA (US); University of Washington, Seattle, WA (US)

( * ) Notice: Subject to any disclaimer, the term of this patent is extended or adjusted under 35 U.S.C. 154(b) by 907 days.

(21) Appl. No.: 09/884,901

(22) Filed: Jun. 18, 2001

(65) Prior Publication Data

US 2002/0076798 A1 Jun. 20, 2002

Related U.S. Application Data

(60) Provisional application No. 60/212,902, filed on Jun. 20, 2000.

(51) Int. Cl.
C07H 21/04 (2006.01)
C12N 15/52 (2006.01)
A61K 31/711 (2006.01)

(52) U.S. Cl. .................. 536/23.2; 536/24.1; 435/320.1; 514/44

(58) Field of Classification Search ..................... None
See application file for complete search history.

(56) References Cited

U.S. PATENT DOCUMENTS

| 6,610,906 B1 * | 8/2003 | Kurachi et al. | 800/25 |
| 6,936,243 B2 * | 8/2005 | Snyder et al. | 424/93.2 |
| 2002/0076798 A1 * | 6/2002 | Miao et al. | 435/226 |

FOREIGN PATENT DOCUMENTS

WO WO 95/11308 A1 4/1995

OTHER PUBLICATIONS

Simonet, W.S. et al., "Long-term Impaired Neutrophil Migration in Mice Overexpressing Human Interleukin-8", 1994, J. Clin. Invest., vol. 94: pp. 1310-1319.*
Kurachi, S. et al., "Role of Intron I in Expression of the Human Factor IX Gene", 1995, J. Biol. Chem., vol. 270: pp. 5276-5281.*
Jallat, S. et al., "Characterization of recombinant human Factor IX expressed in transgenic mice and in derived trans-immortalized hepatic cell lines", 1990, EMBO Journal, vol. 9: pp. 3295-3301.*
Nguyen, HQ et al., "Expression of keratinocyte growth factor in embryonic liver of transgenic mice causes changes in epthelial growth and differentiation resulting in polycystic kidneys and other organ malformations", 1996, Oncogene, vol. 12: pp. 2109-2119.*
Fazio, S. et al. "Type III Hyperlipoproteinemic Phenotype in Transgenic Mice Expressing Dysfunctional Apolipoprotein E", 1993, J. Clin. Invest., vol. 92: pp. 1497-1503.*
Miao, C.H., et al., "A Nonviral Approach: Long-Term and Therapeutic Level Human Factor IX Gene Expression Due to Retention of Optimal HFIX Plasmids in Hepatocytes After Naked DNA Transfer," *Blood* 96(11, 1):210 (Abstract), Nov. 2000.
Miao, C.H., et al., "Inclusion of the Hepatic Locus Control Region, an Intron, and Untranslated Region Increases and Stabilizes Hepatic Factor IX Gene Expression In Vivo but not In Vitro," *Molecular Therapy* 1(6):522-532, Jun. 2000.
Long G.L. et al., *Biochemistry*, 23:4828-37 (1984).
Armentano, D. et al., *Proc. Natl. Acad. Sci. USA*, 87:6141-5 (1990).
Le, M. et al., *Blood*, 89:1254-9 (1997).
Hafenrichter, D.G. et al., *Blood*, 84:3394-404 (1994).
Kaleko, M. et al., *J. Cell. Biochemistry*, 21(A):366 (1995).
Shachter, N.S. et al., *J. Lipid Res.*, 34:1699-707 (1993).
Okuyama, T. et al., *Hum. Gene Ther.*, 7:637-45 (1996).
Simonet, W.S. et al., *J. Biol. Chem.*, 268:8221-9 (1992).
Dang, Q. et al., *J. Biol. Chem.*, 270:22577-85 (1995).
Budker, V. et al., *Gene Ther.*, 3:593-8 (1996).
Liu, F. et al., *Gene Ther.*, 6:1258-1266 (1999).
Zhang, G. et al., *Human Gene Ther.*, 10:1735-1737 (1999).
Brinster et al., "Introns increase transcriptional efficiency in transgenic mice". *PNAs U.S.A*, 85(3):836-40 (1988).
Clayton et al., "Changes in liver-specific compared to common gene transcription during primary culture of mouse hepatocytes", *Mol Cell Biol.*, 3(9):1552-1561 (1983).
Isom et al., "Persistence of liver-specific messenger RNA in cultured hepatocytes: different regulatory events for different genes", *J Cell Biol.*, 105(6 Pt2):2877-85 (1987).
Kay et al., "Direct Hepatic Gene Delivery in Mice results in Persistant Expression of Human Alpha-1-Antitrypsin in vivo", *Human Gene Therapy*, 3:641-647 (1992).
Kay et al., "Expression of human alpha-1-antitrypsin in dogs after autologous transplantation of retroviral transduced hepatocytes", *PNAs U.S.A.*, 89:89-93 (1992).
Kay, M.A. et al., "Therapeutic Serum Concentrations of Human Alpha 1-Antitrypsin after Adrenoviral-Mediated Gene Transfer into Mouse Hepatocytes", *Hepatology*, 21:515-519 (1995).
Palmiter et al., "Heterologous introns can enhance expression of transgenes in mice", *PNAs U S A*, 88(2):478-82 (1991).

* cited by examiner (Continued)

*Primary Examiner*—Joseph Woitach
*Assistant Examiner*—Michael Burkhart
(74) *Attorney, Agent, or Firm*—Perkins Coie LLP

(57) ABSTRACT

In one aspect, the present invention provides nucleic acid expression cassettes that are predominantly expressed in the mammalian liver. The present invention also provides vectors comprising a nucleic acid expression cassette that is predominantly expressed in the mammalian liver. The present invention also provides methods of ameliorating the symptoms of a disease, the methods including the steps of introducing into the liver of a mammalian subject a vector comprising a nucleic acid expression cassette that encodes a polypeptide, and expressing a therapeutic amount of the polypeptide in the liver.

8 Claims, 12 Drawing Sheets

SEQUENCE LISTING

```
<160> NUMBER OF SEQ ID NOS: 18

<210> SEQ ID NO 1
<211> LENGTH: 1438
<212> TYPE: DNA
<213> ORGANISM: HomoSapien

<400> SEQUENCE: 1
gtttgtttcc ttttttaaaa tacattgagt atgcttgcct tttagatata gaaatatctg      60
atgctgtctt cttcactaaa ttttgattac atgatttgac agcaatattg aagagtctaa     120
cagccagcac gcaggttggt aagtactggt tctttgttag ctaggttttc ttcttcttca     180
tttttaaaac taaatagatc gacaatgctt atgatgcatt tatgtttaat aaacactgtt     240
cagttcatga tttggtcatg taattcctgt tagaaaacat tcatctcctt ggtttaaaaa     300
aattaaaagt gggaaaacaa agaaatagca gaatatagtg aaaaaaaata accacattat     360
```

-continued

```
ttttgtttgg acttaccact ttgaaatcaa aatgggaaac aaaagcacaa acaatggcct      420
tatttacaca aaaagtctga ttttaagata tatgacattt caaggtttca gaagtatgta      480
atgaggtgtg tctctaattt tttaaattat atatcttcaa tttaaagttt tagttaaaac      540
ataaagatta acctttcatt agcaagctgt tagttatcac caaagctttt catggattag      600
gaaaaaatca ttttgtctct atgtcaaaca tcttggagtt gatatttggg gaaacacaat      660
actcagttga gttccctagg ggagaaaagc aagcttaaga attgacataa agagtaggaa      720
gttagctaat gcaacatata tcactttgtt ttttcacaac tacagtgact ttatgtattt      780
cccagaggaa ggcatacagg gaagaaatta tcccatttgg acaaacagca tgttctcaca      840
ggaagcattt atcacactta cttgtcaact ttctagaatc aaatctagta gctgacagta      900
ccaggatcag gggtgccaac cctaagcacc cccagaaagc tgactggccc tgtggttccc      960
actccagaca tgatgtcagc tgtgaaatcg acgtcgctgg accataatta ggcttctgtt     1020
cttcaggaga catttgttca aagtcatttg ggcaaccata ttctgaaaac agcccagcca     1080
gggtgatgga tcactttgca agatcctca atgagctatt tcaagtgat gacaaagtgt     1140 gaagttaacc gctcatttga gactttctt tttcatccaa agtaaattca aatatgatta     1200
gaaatctgac cttttattac tggaattctc ttgactaaaa gtaaattga attttaattc     1260 ctaaatctcc atgtgtatac agtactgtgg gaacatcaca gattttggct ccatgcccta     1320
aagagaaatt ggctttcaga ttatttggat taaaaacaaa gactttctta agagatgtaa     1380
aattttcatg atgtttctt ttttgctaaa actaagaat tattcttta catttcag      1438
```

<210> SEQ ID NO 2
<211> LENGTH: 1413
<212> TYPE: DNA
<213> ORGANISM: HomoSapien
<220> FEATURE:
<221> NAME/KEY: CDS
<222> LOCATION: (30)..(1412)

<400> SEQUENCE: 2

```
accactttca caatctgcta gcaaaggtt atg cag cgc gtg aac atg atc atg            53
                                Met Gln Arg Val Asn Met Ile Met
                                 1               5 gca gaa tca cca ggc ctc atc acc atc tgc ctt tta gga tat cta ctc           101
Ala Glu Ser Pro Gly Leu Ile Thr Ile Cys Leu Leu Gly Tyr Leu Leu
     10              15                  20 agt gct gaa tgt aca gtt ttt ctt gat cat gaa aac gcc aac aaa att           149
Ser Ala Glu Cys Thr Val Phe Leu Asp His Glu Asn Ala Asn Lys Ile
25              30                  35                  40 ctg aat cgg cca aag agg tat aat tca ggt aaa ttg gaa gag ttt gtt           197
Leu Asn Arg Pro Lys Arg Tyr Asn Ser Gly Lys Leu Glu Glu Phe Val
                 45                  50                  55 caa ggg aac ctt gag aga gaa tgt atg gaa gaa aag tgt agt ttt gaa           245
Gln Gly Asn Leu Glu Arg Glu Cys Met Glu Glu Lys Cys Ser Phe Glu
             60                  65                  70 gaa gca cga gaa gtt ttt gaa aac act gaa aga aca act gaa ttt tgg           293
Glu Ala Arg Glu Val Phe Glu Asn Thr Glu Arg Thr Thr Glu Phe Trp
         75                  80                  85 aag cag tat gtt gat gga gat cag tgt gag tcc aat cca tgt tta aat           341
Lys Gln Tyr Val Asp Gly Asp Gln Cys Glu Ser Asn Pro Cys Leu Asn
         90                  95                 100 ggc ggc agt tgc aag gat gac att aat tcc tat gaa tgt tgg tgt ccc           389
Gly Gly Ser Cys Lys Asp Asp Ile Asn Ser Tyr Glu Cys Trp Cys Pro
105                 110                 115                 120
```

```
ttt gga ttt gaa gga aag aac tgt gaa tta gat gta aca tgt aac att     437
Phe Gly Phe Glu Gly Lys Asn Cys Glu Leu Asp Val Thr Cys Asn Ile
                125                 130                 135 aag aat ggc aga tgc gag cag ttt tgt aaa aat agt gct gat aac aag     485
Lys Asn Gly Arg Cys Glu Gln Phe Cys Lys Asn Ser Ala Asp Asn Lys
        140                 145                 150 gtg gtt tgc tcc tgt act gag gga tat cga ctt gca gaa aac cag aag     533
Val Val Cys Ser Cys Thr Glu Gly Tyr Arg Leu Ala Glu Asn Gln Lys
            155                 160                 165 tcc tgt gaa cca gca gtg cca ttt cca tgt gga aga gtt tct gtt tca     581
Ser Cys Glu Pro Ala Val Pro Phe Pro Cys Gly Arg Val Ser Val Ser
                170                 175                 180 caa act tct aag ctc acc cgt gct gag gct gtt ttt cct gat gtg gac     629
Gln Thr Ser Lys Leu Thr Arg Ala Glu Ala Val Phe Pro Asp Val Asp
185                 190                 195                 200 tat gta aat tct act gaa gct gaa acc att ttg gat aac atc act caa     677
Tyr Val Asn Ser Thr Glu Ala Glu Thr Ile Leu Asp Asn Ile Thr Gln
            205                 210                 215 agc acc caa tca ttt aat gac ttc act cgg gtt gtt ggt gga gaa gat     725
Ser Thr Gln Ser Phe Asn Asp Phe Thr Arg Val Val Gly Gly Glu Asp
                220                 225                 230 gcc aaa cca ggt caa ttc cct tgg cag gtt gtt ttg aat ggg aaa gtt     773
Ala Lys Pro Gly Gln Phe Pro Trp Gln Val Val Leu Asn Gly Lys Val
                235                 240                 245 gat gca ttc tgt gga ggc tct atc gtt aat gaa aaa tgg att gta act     821
Asp Ala Phe Cys Gly Gly Ser Ile Val Asn Glu Lys Trp Ile Val Thr
            250                 255                 260 gct gcc cac tgt gtt gaa act ggt gtt aaa att aca gtt gtc gca ggt     869
Ala Ala His Cys Val Glu Thr Gly Val Lys Ile Thr Val Val Ala Gly
265                 270                 275                 280 gaa cat aat att gag gag aca gaa cat aca gag caa aag cga aat gtg     917
Glu His Asn Ile Glu Glu Thr Glu His Thr Glu Gln Lys Arg Asn Val
                285                 290                 295 att cga att att cct cac cac aac tac aat gca gct att aat aag tac     965
Ile Arg Ile Ile Pro His His Asn Tyr Asn Ala Ala Ile Asn Lys Tyr
                300                 305                 310 aac cat gac att gcc ctt ctg gaa ctg gac gaa ccc tta gtg cta aac    1013
Asn His Asp Ile Ala Leu Leu Glu Leu Asp Glu Pro Leu Val Leu Asn
            315                 320                 325 agc tac gtt aca cct att tgc att gct gac aag gaa tac acg aac atc    1061
Ser Tyr Val Thr Pro Ile Cys Ile Ala Asp Lys Glu Tyr Thr Asn Ile
                330                 335                 340 ttc ctc aaa ttt gga tct ggc tat gta agt ggc tgg gga aga gtc ttc    1109
Phe Leu Lys Phe Gly Ser Gly Tyr Val Ser Gly Trp Gly Arg Val Phe
345                 350                 355                 360 cac aaa ggg aga tca gct tta gtt ctt cag tac ctt aga gtt cca ctt    1157
His Lys Gly Arg Ser Ala Leu Val Leu Gln Tyr Leu Arg Val Pro Leu
                365                 370                 375 gtt gac cga gcc aca tgt ctt cga tct aca aag ttc acc atc tat aac    1205
Val Asp Arg Ala Thr Cys Leu Arg Ser Thr Lys Phe Thr Ile Tyr Asn
            380                 385                 390 aac atg ttc tgt gct ggc ttc cat gaa gga ggt aga gat tca tgt caa    1253
Asn Met Phe Cys Ala Gly Phe His Glu Gly Gly Arg Asp Ser Cys Gln
                395                 400                 405 gga gat agt ggg gga ccc cat gtt act gaa gtg gaa ggg acc agt ttc    1301
Gly Asp Ser Gly Gly Pro His Val Thr Glu Val Glu Gly Thr Ser Phe
410                 415                 420 tta act gga att att agc tgg ggt gaa gag tgt gca atg aaa ggc aaa    1349
Leu Thr Gly Ile Ile Ser Trp Gly Glu Glu Cys Ala Met Lys Gly Lys
```

```
                425                 430                 435                 440
tat gga ata tat acc aag gta tcc cgg tat gtc aac tgg att aag gaa              1397
Tyr Gly Ile Tyr Thr Lys Val Ser Arg Tyr Val Asn Trp Ile Lys Glu
                    445                 450                 455 aaa aca aag ctc act t                                                        1413
Lys Thr Lys Leu Thr
            460

<210> SEQ ID NO 3
<211> LENGTH: 461
<212> TYPE: PRT
<213> ORGANISM: HomoSapien

<400> SEQUENCE: 3

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
```

-continued

```
                  325                 330                 335
Ala Asp Lys Glu Tyr Thr Asn Ile Phe Leu Lys Phe Gly Ser Gly Tyr
              340                 345                 350

Val Ser Gly Trp Gly Arg Val Phe His Lys Gly Arg Ser Ala Leu Val
          355                 360                 365

Leu Gln Tyr Leu Arg Val Pro Leu Val Asp Arg Ala Thr Cys Leu Arg
      370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                  405                 410                 415

Thr Glu Val Glu Gly Thr Ser Phe Leu Thr Gly Ile Ile Ser Trp Gly
              420                 425                 430

Glu Glu Cys Ala Met Lys Gly Lys Tyr Gly Ile Tyr Thr Lys Val Ser
          435                 440                 445

Arg Tyr Val Asn Trp Ile Lys Glu Lys Thr Lys Leu Thr
      450                 455                 460
```

<210> SEQ ID NO 4
<211> LENGTH: 771
<212> TYPE: DNA
<213> ORGANISM: HomoSapien

<400> SEQUENCE: 4

```
caggctcaga ggcacacagg agtttctggg ctcaccctgc cccttccaa ccctcagtt      60
cccatcctcc agcagctgtt tgtgtgctgc ctctgaagtc cacactgaac aaacttcagc     120
ctactcatgt ccctaaaatg gcaaacatt gcaagcagca acagcaaac acacagccct      180
ccctgcctgc tgaccttgga gctggggcag aggtcagaga cctctctggg cccatgccac     240
ctccaacatc cactcgaccc cttggaattt cggtggagag gagcagaggt tgtcctggcg     300
tggtttaggt agtgtgagag ggtccgggtt caaaaccact tgctgggtgg ggagtcgtca     360
gtaagtggct atgccccgac cccgaagcct gtttccccat ctgtacaatg gaaatgataa     420
agacgcccat ctgatagggt ttttgtggca aataaacatt tggtttttt gttttgtttt     480
gttttgtttt ttgagatgga ggtttgctct gtcgcccagg ctggagtgca gtgacacaat     540
ctcatctcac cacaaccttc ccctgcctca gcctcccaag tagctgggat tacaagcatg     600
tgccaccaca cctggctaat tttctatttt tagtagagac gggtttctcc atgttggtca     660
gcctcagcct cccaagtaac tgggattaca ggcctgtgcc accacaccg gctaattttt     720
tctattttg acagggacgg ggtttcacca tgttggtcag gctcctctag a              771
```

<210> SEQ ID NO 5
<211> LENGTH: 418
<212> TYPE: DNA
<213> ORGANISM: HomoSapien

<400> SEQUENCE: 5

```
ggatcttgct accagtggaa cagccactaa ggattctgca gtgagagcag agggccagct      60
aagtggtact ctcccagaga ctgtctgact cacgccaccc cctccacctt ggacacagga    120
cgctgtggtt tctgagccag gtacaatgac tcctttcggt aagtgcagtg gaagctgtac    180
actgcccagg caaagcgtcc gggcagcgta ggcgggcgac tcagatccca gccagtggac    240
ttagcccctg tttgctcctc cgataactgg ggtgaccttg gttaatattc accagcagcc    300
tcccccgttg cccctctgga tccactgctt aaatacggac gaggacaggg ccctgtctcc    360
```

```
tcagcttcag gcaccaccac tgacctggga cagtgaatga tccccctgat ctgcggcc        418

<210> SEQ ID NO 6
<211> LENGTH: 282
<212> TYPE: DNA
<213> ORGANISM: Bos taurus

<400> SEQUENCE: 6 cccggggat  cagcctcgac  tgtgccttct  agttgccagc  catctgttgt  ttgcccctcc    60
cccgtgcctt  ccttgaccct  ggaaggtgcc  actcccactg  tcctttccta  ataaaatgag   120
gaaattgcat  cgcattgtct  gagtaggtgt  cattctattc  tgggggtgg   ggtggggcag   180 gacagcaagg  gggaggattg  ggaagacaat  agcaggcatg  ctggggatgc  ggtgggctct   240
atggcttctg  aggcggaaag  aaccagctgg  ggctcgagat  cc                      282

<210> SEQ ID NO 7
<211> LENGTH: 1707
<212> TYPE: DNA
<213> ORGANISM: HomoSapien

<400> SEQUENCE: 7
aatgaaagat  ggatttccaa  ggttaattca  ttggaattga  aaattaacag  ggcctctcac    60
taactaatca  ctttcccatc  ttttgttaga  tttgaatata  tacattctat  gatcattgct   120
ttttctcttt  acaggggaga  atttcatatt  ttacctgagc  aaattgatta  gaaaatggaa   180
ccactagagg  aatataatgt  gttaggaaat  tacagtcatt  tctaagggcc  cagcccttga   240
caaaattgtg  aagttaaatt  ctccactctg  tccatcagat  actatggttc  tccactatgg   300
caactaactc  actcaatttt  ccctccttag  cagcattcca  tcttcccgat  cttctttgct   360
tctccaacca  aaacatcaat  gtttattagt  tctgtataca  gtacaggatc  tttggtctac   420
tctatcacaa  ggccagtacc  acactcatga  agaaagaaca  caggagtagc  tgagaggcta   480
aaactcatca  aaacactac   tccttttcct  ctaccctatt  cctcaatctt  ttacctttc    540 caaatcccaa  tccccaaatc  agtttttctc  tttcttactc  cctctctccc  ttttaccctc   600
catggtcgtt  aaaggagaga  tggggagcat  cattctgtta  tacttctgta  cacagttata   660
catgtctatc  aaacccagac  ttgcttccat  agtggagact  tgcttttcag  aacataggga   720
tgaagtaagg  tgcctgaaaa  gtttggggga  aaagtttctt  tcagagagtt  aagttatttt   780
atatatataa  tatatatata  aaatatataa  tatacaatat  aaatatatag  tgtgtgtgtg   840
tatgcgtgtg  tgtagacaca  cacgcataca  cacatataat  ggaagcaata  agccattcta   900
agagcttgta  tggttatgga  ggtctgacta  ggcatgattt  cacgaaggca  agattggcat   960
atcattgtaa  ctaaaaaagc  tgacattgac  ccagacatat  tgtactcttt  ctaaaaataa  1020
taataataat  gctaacagaa  agaagagaac  cgttcgtttg  caatctacag  ctagtagaga  1080
ctttgaggaa  gaattcaaca  gtgtgtcttc  agcagtgttc  agagccaagc  aagaagttga  1140
agttgcctag  accagaggac  ataagtatca  tgtctccttt  aactagcata  ccccgaagtg  1200
gagaagggtg  cagcaggctc  aaaggcataa  gtcattccaa  tcagccaact  aagttgtcct  1260
tttctggttt  cgtgttcacc  atggaacatt  ttgattatag  ttaatccttc  tatcttgaat  1320
cttctagaga  gttgctgacc  aactgacgta  tgtttccctt  tgtgaattaa  taaactggtg  1380
ttctggttca  taccttggct  ttttgtggat  tccattgatg  tgaatcagtc  accctgtatt  1440
tgatgatgca  tgggactact  gacaaaatca  ctctgaccct  gccaagctgc  tgccttctcc  1500
```

```
tgccccaacc tcaccccag ccaggcctca ctcttgctag ttcctttagt tcttttagtc    1560
aatatatttt tgtcttcgca tataagtata aataaacata tttttaaatt tcttggctgg    1620
gcccagtggc tcacgcctat aatcccagca cttctggagg ccaaggtggg cggatcacct    1680
gaggttagga gtttcaggcc aagctta                                        1707

<210> SEQ ID NO 8
<211> LENGTH: 154
<212> TYPE: DNA
<213> ORGANISM: HomoSapien

<400> SEQUENCE: 8
gtttgtgtgc tgcctctgaa gtccacactg aacaaacttc agcctactca tgtccctaaa    60
atgggcaaac attgcaagca gcaaacagca aacacacagc cctccctgcc tgctgacctt    120
ggagctgggg cagaggtcag agacctctct gggc                                154

<210> SEQ ID NO 9
<211> LENGTH: 328
<212> TYPE: DNA
<213> ORGANISM: Homo Sapien

<400> SEQUENCE: 9
caggctcaga ggcacacagg agtttctggg ctcaccctgc cccttccaa cccctcagtt     60 cccatcctcc agcagctgtt tgtgtgctgc ctctgaagtc cacactgaac aaacttcagc    120
ctactcatgt ccctaaaatg gcaaacatt gcaagcagca aacagcaaac acacagccct    180
ccctgcctgc tgaccttgga gctggggcag aggtcagaga cctctctggg cccatgccac    240
ctccaacatc cactcgaccc cttggaattt cggtggagag gagcagaggt tgtcctggcg    300
tggtttaggt agtgtgagag ggtccggg                                       328

<210> SEQ ID NO 10
<211> LENGTH: 8
<212> TYPE: DNA
<213> ORGANISM: Artificial Sequence
<220> FEATURE:
<221> NAME/KEY: misc_feature
<223> OTHER INFORMATION: HNF-1 Hepatic Nuclear Factor Binding Site
      Consensus Sequence

<400> SEQUENCE: 10 tgtaacag                                                             8

<210> SEQ ID NO 11
<211> LENGTH: 22
<212> TYPE: DNA
<213> ORGANISM: Artificial Sequence
<220> FEATURE:
<221> NAME/KEY: misc_feature
<223> OTHER INFORMATION: HNF-1 Alternative Hepatic Nuclear Factor
      Binding Site Consensus Sequence

<400> SEQUENCE: 11
cacggataaa tatgaacctt gg                                             22

<210> SEQ ID NO 12
<211> LENGTH: 11
<212> TYPE: DNA
<213> ORGANISM: Artificial Sequence
<220> FEATURE:
<221> NAME/KEY: misc_feature
<223> OTHER INFORMATION: HNF-3alpha Hepatic Nuclear Binding Site
      Consensus Sequence
```

<400> SEQUENCE: 12
tattgayttw g                                                          11

<210> SEQ ID NO 13
<211> LENGTH: 10
<212> TYPE: DNA
<213> ORGANISM: Artificial Sequence
<220> FEATURE:
<221> NAME/KEY: misc_feature
<223> OTHER INFORMATION: HNF-3beta Hepatic Nuclear Binding Site
      Consensus Sequence

<400> SEQUENCE: 13
atattgattt                                                            10

<210> SEQ ID NO 14
<211> LENGTH: 10
<212> TYPE: DNA
<213> ORGANISM: Artificial Sequence
<220> FEATURE:
<221> NAME/KEY: misc_feature
<223> OTHER INFORMATION: HNF-4 Hepatic Nuclear Binding Site Consensus
      Sequence

<400> SEQUENCE: 14 aagycaayha                                                            10

<210> SEQ ID NO 15
<211> LENGTH: 10
<212> TYPE: DNA
<213> ORGANISM: Artificial Sequence
<220> FEATURE:
<221> NAME/KEY: misc_feature
<223> OTHER INFORMATION: HNF-6 Hepatic Nuclear Binding Site Consensus
      Sequence

<400> SEQUENCE: 15
aaatcaattt                                                            10

<210> SEQ ID NO 16
<211> LENGTH: 13
<212> TYPE: DNA
<213> ORGANISM: Artificial Sequence
<220> FEATURE:
<221> NAME/KEY: misc_feature
<223> OTHER INFORMATION: HNF-6 Alternative Hepatic Nuclear Binding Site
      Consensus Sequence

<400> SEQUENCE: 16
attattgata aaa                                                        13

<210> SEQ ID NO 17
<211> LENGTH: 30
<212> TYPE: DNA
<213> ORGANISM: Artificial Sequence
<220> FEATURE:
<221> NAME/KEY: misc_feature
<223> OTHER INFORMATION: Human Factor IX cDNA Primer Consensus Sequence

<400> SEQUENCE: 17
gatggagatc agtgtgagtc caatccatgt                                      30

<210> SEQ ID NO 18
<211> LENGTH: 30
<212> TYPE: DNA
<213> ORGANISM: Artificial Sequence

```
<220> FEATURE:
<221> NAME/KEY: misc_feature
<223> OTHER INFORMATION: Human Factor IX cDNA Primer Consensus Sequence

<400> SEQUENCE: 18
agccacttac atagccagat ccaaatttga                                              30
```

LIVER-SPECIFIC GENE EXPRESSION CASSETTES, AND METHODS OF USE

RELATED APPLICATIONS

This application claims the benefit of priority of U.S. Provisional Patent Application Ser. No. 60/212,902, filed on Jun. 20, 2000, under 35 U.S.C. § 119.

GOVERNMENT RIGHTS

This invention was funded, in part, by National Institutes of Health Grant Numbers HL53682, DK49022, and NIH-NRSA HL09754. The United States government has certain rights in this invention.

FIELD OF THE INVENTION

This invention relates to nucleic acid constructs and vectors useful for expression of nucleic acid molecules and/or proteins in mammalian liver cells.

BACKGROUND OF THE INVENTION

One goal in the area of gene therapy is to develop expression cassettes and vectors that are capable of expressing a nucleic acid molecule, such as an antisense molecule, and/or a polypeptide for extended periods of time within a desired cell, tissue, or organ. Preferably, these cassettes and vectors will not trigger an immune response in the body of a subject. The expression cassettes and vectors will therefore be able to provide a therapeutic dose of a polypeptide or nucleic acid molecule for an extended time period.

Preferably, expression cassettes can be included in any type of vector used in gene therapy, such as vectors that integrate into a host cell genome, and episomal vectors that do not integrate into a host cell genome.

SUMMARY OF THE INVENTION

In one aspect, the present invention provides nucleic acid expression cassettes that are predominantly expressed in the mammalian liver. The expression cassettes of this aspect of the invention comprise: (a) an hepatic locus control element; (b) an hepatic promoter located 3' to the hepatic locus control element; (c) a coding sequence located 3' to the hepatic promoter, said coding sequence encoding a polypeptide; (d) a polyadenylation signal located 3' to the coding sequence; and (e) an intron located 3' to the hepatic promoter and 5' to the polyadenylation signal, wherein elements (a), (b), (c), (d) and (e) are operably linked to express the polypeptide encoded by the coding sequence. In some embodiments, the expression cassettes of the invention direct expression of a therapeutic amount of a polypeptide in liver cells for a period of at least 100 days (such as at least 200 days, at least 300 days, at least 400 days, or at least 500 days).

In another aspect, the present invention provides vectors that comprise a nucleic acid expression cassette that is predominantly expressed in the mammalian liver. The expression cassette of the vectors comprises: (a) an hepatic locus control element; (b) an hepatic promoter located 3' to the hepatic locus control element; (c) a coding sequence located 3' to the hepatic promoter, said coding sequence encoding a polypeptide; (d) a polyadenylation signal located 3' to the coding sequence; and (e) an intron located 3' to the hepatic promoter and 5' to the polyadenylation signal, wherein elements (a), (b), (c), (d) and (e) are operably linked to express the polypeptide encoded by the coding sequence. Some vectors of the invention are episomal vectors, and some vectors of the inventions are integrating vectors such as integrating viral vectors.

In another aspect, the present invention provides methods of ameliorating the symptoms of a disease. The methods of this aspect of the invention comprise the steps of: (1) introducing into the liver of a mammalian subject a vector comprising a nucleic acid expression cassette, said expression cassette comprising: (a) an hepatic locus control element; (b) an hepatic promoter located 3' to the hepatic locus control element; (c) a coding sequence located 3' to the hepatic promoter, said coding sequence encoding a polypeptide; (d) a polyadenylation signal located 3' to the coding sequence; (e) an intron located 3' to the hepatic promoter and 5' to the polyadenylation signal, wherein elements (a), (b), (c), (d) and (e) are operably linked to express the polypeptide encoded by the coding sequence; and (2) expressing a therapeutic amount of said polypeptide in the liver. Representative examples of polypeptides that can be expressed utilizing the methods of this aspect of the invention are blood clotting factors, such as Factor IX. In some embodiments of the methods of this aspect of the invention, a therapeutic amount of the polypeptide is expressed for at least 100 days (such as at least 200 days, at least 300 days, at least 400 days, and at least 500 days).

The cassettes, vectors, and methods of the invention are useful, for example, for expressing a desired polypeptide in mammalian liver cells. In some embodiments, the expressed polypeptide(s) ameliorates one or more symptoms of a disease. For example, the cassettes, vectors, and methods of the invention can be used to express the Factor IX blood clotting protein to compensate for a deficiency of that protein in the host organism.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
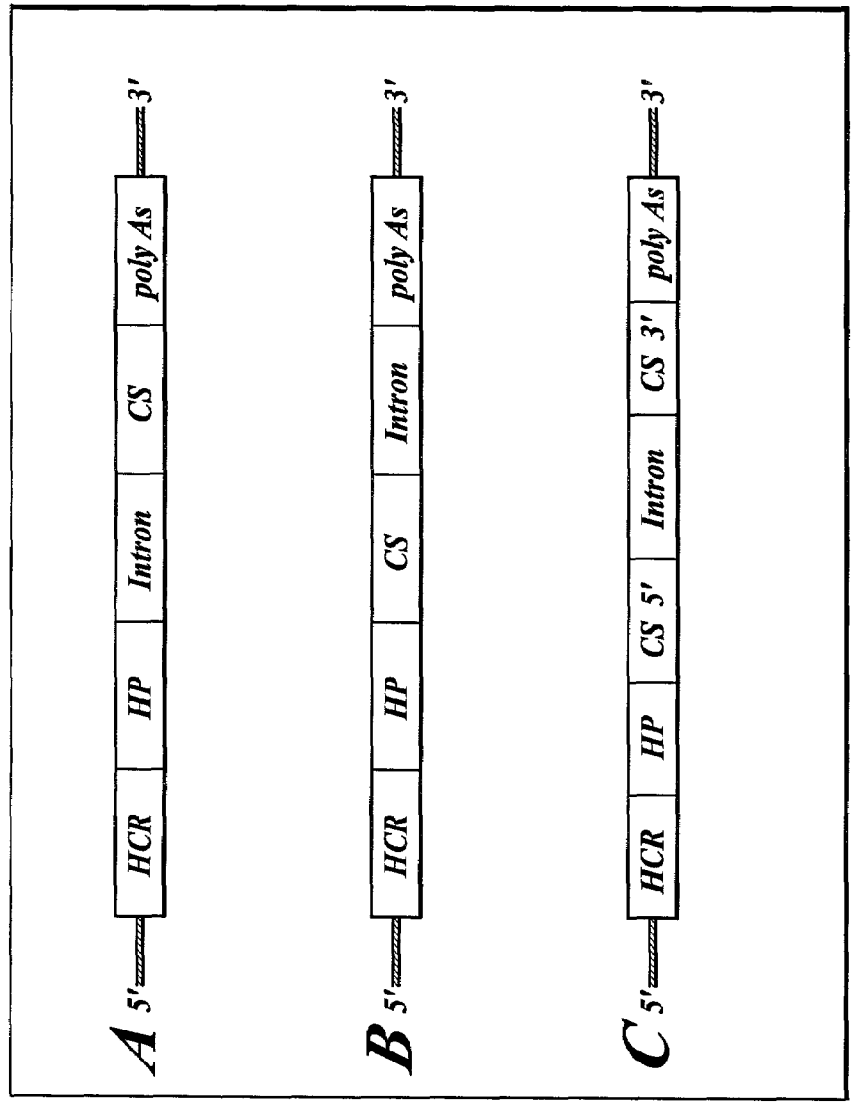
FIG. 1A shows the structure of an embodiment of the expression cassettes of the invention in which Factor IX Intron A (SEQ ID NO: 1) is located 5' to the coding sequence of the human Factor IX cDNA molecule (SEQ ID NO: 2), encoding the Factor IX protein (SEQ ID NO: 3). HCR, hepatic locus control region (SEQ ID NO: 4); HP, human alpha1 antitrypsin promoter (SEQ ID NO: 5); CS, Factor IX coding sequence (SEQ ID NO: 2); polyAs, polyadenylation signal (SEQ ID NO: 6).
FIG. 1B shows the structure of an expression cassette of the invention in which the intron (SEQ ID NO: 1) is located 3' to the coding sequence of the human Factor IX cDNA molecule (SEQ ID NO: 2). The abbreviations are as set forth in the legend to FIG. 1A.
FIG. 1C shows the structure of an expression cassette of the invention in which the intron (SEQ ID NO: 1) is located within the coding sequence of the human Factor IX cDNA molecule (SEQ ID NO: 2). The abbreviations are as set forth in the legend for FIG. 1A.

Unless specifically defined herein, all terms used herein have the same meaning as they would to one skilled in the art of the present invention. Practitioners are particularly directed to Sambrook et al., *Molecular Cloning: A Laboratory Manual*, 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art.

The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. Typically, stringent hybridization conditions are no more than 25° C. to 30° C. (for example, 10° C.) below the melting temperature (Tm) of the native duplex. By way of non-limiting example, representative salt and temperature conditions for achieving stringent hybridization are: 1×SSC, 0.5% SDS at 65° C. A representative time period for achieving hybridization is 12 hours. (See generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987).

Tm for nucleic acid molecules greater than about 100 bases can be calculated by the formula Tm=81.5+0.41%(G+C)−log(Na+). For oligonucleotide molecules less than 100 bases in length, exemplary hybridization conditions are 5 to 10° C. below Tm. On average, the Tm of a short oligonucleotide duplex is reduced by approximately (500/oligonucleotide length)° C. For example, a 14 base oligonucleotide is hybridized at room temperature, 17 bases at 37° C., 20 bases at 42° C., and 23 bases at 48° C.

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The term "vector" refers to a nucleic acid molecule, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated.

As used herein, the term "nucleic acid expression cassette" refers to a nucleic acid molecule that includes one or more transcriptional control elements (such as promoters and enhancers) that direct gene expression in one or more desired cell types, tissues or organs.

In one aspect, the present invention provides nucleic acid expression cassettes that are predominantly expressed in the mammalian liver. The expression cassettes of this aspect of the invention comprise the following elements: (a) an hepatic locus control element; (b) an hepatic promoter located 3' to the hepatic locus control element; (c) a coding sequence located 3' to the hepatic promoter, said coding sequence encoding a polypeptide; (d) a polyadenylation signal located 3' to the coding sequence; and (e) an intron located 3' to the hepatic promoter and 5' to the polyadenylation signal, wherein elements (a), (b), (c), (d) and (e) are operably linked to express the polypeptide encoded by the coding sequence.

The nucleic acid expression cassettes of this aspect of the invention are predominantly expressed in the liver, i.e., at least 50% of the expression of the encoded nucleic acid molecule or polypeptide occurs within the liver. More typically, at least 90% of the expression occurs within the liver. Some of the expression cassettes of this aspect of the invention are exclusively expressed within the liver. Representative embodiments of expression cassettes of this aspect of the invention are shown in FIG. 1. The expression cassette shown in FIG. 1A includes the following contiguous elements arranged from 5' to 3': An hepatic locus control element consisting of the nucleic acid sequence set forth in SEQ ID NO: 4 (the nucleic acid sequence set forth in SEQ ID NO: 9 is also useful); the human alpha antitrypsin promoter consisting of the nucleic acid sequence set forth in SEQ ID NO: 5; the intron consisting of the nucleic acid sequence set forth in SEQ ID NO: 1; the nucleic acid sequence set forth in SEQ ID NO: 2 encoding the Factor IX polypeptide having the amino acid sequence set forth in SEQ ID NO: 3; and the polyadenylation signal consisting of the nucleic acid sequence set forth in SEQ ID NO: 6. FIG. 1B shows a representative expression cassette of the invention identical to the expression cassette shown in FIG. 1B, except that the intron (SEQ ID NO: 1) is located 3' to the coding sequence (SEQ ID NO: 2). FIG. 1C shows a representative expression cassette of the invention identical to the expression cassette shown in FIG. 1A, except that the intron (SEQ ID NO: 1) is located within the coding sequence (SEQ ID NO: 2).

Hepatic locus control elements useful in the expression cassettes of the invention are capable of enhancing the expression of nucleic acid molecules in liver cells, and confer copy number dependent, position independent expression on the expression cassette. Some hepatic locus control regions useful in the expression cassettes of the invention include a matrix attachment region and/or a liver-specific enhancer element. While not wishing to be bound by theory, hepatic locus control regions useful in the expression cassettes of the invention may maintain chromatin in a transcriptionally active state which is typically indicated by the presence of DNaseI hypersensitive sites. Some hepatic locus control elements useful in the expression cassettes of the invention hybridize under stringent conditions to the complement of the hepatic locus control element consisting of the nucleic acid sequence set forth in SEQ ID NO: 4. The nucleic acid sequences of exemplary hepatic locus control elements useful in the practice of the invention are set forth in SEQ ID NO: 4 and SEQ ID NO: 9. Other useful hepatic locus control elements are described in Simonet, W. -S., et al., J. Biol. Chem. 268(11):8221-8229 (1993), and in Allan, C. M., et al., J. Biol. Chem. 270(44):26278-26281 (1995).

Hepatic promoters useful in the expression cassettes of the invention are capable of directing expression of nucleic acid molecules in liver cells. Typically, hepatic promoters are active predominantly or exclusively in liver cells. In this context, the term "predominantly" means that at least 50% of the hepatic promoter expression, more typically at least 90% of the hepatic promoter expression (such as 100% of the hepatic promoter expression) occurs in liver cells. Some hepatic promoters useful in the expression cassettes of the invention hybridize under stringent conditions to the complement of the hepatic promoter consisting of the nucleic acid sequence set forth in SEQ ID NO: 5. Some hepatic promoters useful in the expression cassettes of the invention include at least one, typically several, hepatic nuclear factor binding sites, such as the hepatic nuclear factor binding sites set forth in SEQ ID NOs: 10-16. Hepatic promoters useful in the expression cassettes of the invention can be constitutive or inducible promoters. Representative examples of hepatic promoters useful in the expression cassettes of the invention include: The albumin promoter, the HBV promoter, the α1-antitrypsin promoter (SEQ ID NO: 5) and the human Factor IX promoter.

The coding sequence included within the expression cassettes of the invention can encode any desired polypeptide, including, but not limited to, biologically active polypeptides, such as blood clotting proteins. Examples 3 and 4 herein describe the expression of the Factor IX blood clotting protein in mouse liver. The expression cassettes of the invention can be used, for example, to express proteins that are normally expressed and utilized in the liver, such as Factor IX protein, or to express proteins that are expressed in the liver and are then exported to the blood stream for transport to other portions of the body. Thus, in some embodiments, the expression cassettes of the invention can be used to express a therapeutic amount of a polypeptide to ameliorate the symptoms of a disease. Again, by way of non-limiting example, the expression cassettes of the invention can be used to express proteins synthesized by viruses that infect liver cells, thereby permitting the function of the viral protein to be determined.

Any intron can be utilized in the expression cassettes of the invention. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene to that encodes the protein that is encoded by the coding sequence within the expression cassette. Thus, for example, in the vectors described in Examples 3 and 4, the coding sequence encodes Factor IX polypeptide, and the intron is a portion of the first intron of the Factor IX gene (SEQ ID NO: 1). The intron can be located 5' to the coding sequence, 3' to the coding sequence, or within the coding sequence. An advantage of locating the intron 5' to the coding sequence is to minimize the chance of the intron interfering with the function of the polyadenylation signal.

Any polyadenylation signal that directs the synthesis of a poly A tail is useful in the expression cassettes of the invention. Some polyadenylation signals useful in the expression cassettes of the invention hybridize under stringent conditions to the polyadenylation signal consisting of the nucleic acid sequence set forth in SEQ ID NO: 6.

The nucleic acid expression cassettes of the invention direct the expression of a therapeutic amount of the polypeptide encoded by the coding sequence within the expression cassette. A therapeutic amount is an amount that ameliorates the symptoms of a disease. The expression cassettes of the invention direct the expression of a therapeutic amount of the polypeptide encoded by the coding sequence for an extended period, typically greater than 200 days, and in some instances greater than 500 days. Expression of the polypeptide encoded by the coding sequence can be measured by any art-recognized means, such as by antibody-based assays, such as a Western Blot or an ELISA assay. Again, by way of non-limiting example, expression of the polypeptide encoded by the coding sequence within the expression cassette can be measured in a bioassay that detects an enzymatic or biological activity of the polypeptide.

In another aspect, the present invention provides vectors that include an expression cassette of the invention. The vectors can be episomal vectors (i.e., that do not integrate into the genome of a host cell), or can be vectors that integrate into the host cell genome. Examples of episomal vectors include plasmids, and examples of vector that integrate into the host cell genome include viral vectors. Representative plasmid vectors include pUC vectors, bluescript vectors and pBR322. Representative viral vectors include adeno-associated virus, adenovirus, retroviruses and lentiviruses.

For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (A. D. Miller, *Hum. Gen. Ther.* 1:5-14 (1990)).

Adenoviral vectors are designed to be administered directly to a living subject. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, *Adv. Drug Del. Rev.* 12:185-199 (1993)).

Another viral vector is the herpes simplex virus, a large, double-stranded DNA virus. Recombinant forms of the vaccinia virus can accommodate large inserts and are generated by homologous recombination. To date, this vector has been used to deliver interleukins (ILs), such as human IL-1β and the costimulatory molecules B7-1 and B7-2 (G. R. Peplinski et al., *Ann. Surg. Oncol.* 2:151-9 (1995); J. W. Hodge et al., *Cancer Res.* 54:5552-55 (1994)).

Another approach to gene therapy involves the direct introduction of DNA plasmids into living subjects. (F. D. Ledley, *Hum. Gene Ther.* 6:1129-1144 (1995)). The plasmid DNA is taken up by cells within the body and can direct expression of recombinant proteins. In some cases, plasmid DNA is delivered to cells in the form of liposomes in which the DNA is associated with one or more lipids, such as DOTMA (1,2,-diolcyloxypropyl-3-trimethyl ammonium bromide) and DOPE (dioleoylphosphatidylethanolamine). Formulations with DOTMA have been shown to provide expression in pulmonary epithelial cells in animal models (K. L. Brigham et al., *Am. J. Med. Sci.,* 298:278-281 (1989); A. B. Canonico et al., *Am. J. Respir. Cell. Mol. Biol.* 10:24-29 (1994)). Additionally, studies have demonstrated that intramuscular injection of plasmid DNA formulated with 5% PVP (50,000 kDa) increases the level of reporter gene expression in muscle as much as 200-fold over the levels found with injection of DNA in saline alone (R. J. Mumper et al., *Pharm. Res.* 13:701-709 (1996); R. J. Mumper et al., *Proc. Intern. Symp. Cont. Rol. Bioac. Mater.* 22:325-326 (1995)). Intramuscular administration of plasmid DNA results in gene expression that lasts for many months (J. A. Wolff et al., *Hum. Mol. Genet.* 1:363-369 (1992); M. Manthorpe et al., *Hum. Gene Ther.* 4:419-431 (1993); G. Ascadi et al., *New Biol.* 3:71-81 (1991), D. Gal et al., *Lab. Invest.* 68:18-25 (1993)).

Gene expression has been observed after interstitial injection into liver (M. A. Hickman et al., *Hum. Gene Ther.* 5:1477-1483 (1994)), skin (E. Raz et al., *Proc. Natl. Acad. Sci.* 91:9519-9523 (1994)), instillation into the airways (K. B. Meyer et al., *Gene Therapy* 2:450-460 (1995)), application to the endothelium (G. D. Chapman et al., *Circulation Res.* 71:27-33 (1992); R. Riessen et al., *Human Gene Therapy,* 4:749-758 (1993)), and after intravenous administration (R. M. Conry et al., *Cancer Res.* 54:1164-1168 (1994)).

Various devices have been developed for enhancing the availability of DNA to the target cell. A simple approach is to contact the target cell physically with catheters or implantable materials containing DNA (G. D. Chapman et al., *Circulation Res.* 71:27-33 (1992)). Another approach is to utilize needle-free, jet injection devices which project a column of liquid directly into the target tissue under high pressure. (P. A. Furth et al., *Anal Biochem.* 20:365-368 (1992); (H. L. Vahlsing et al., *J. Immunol. Meth.* 175:11-22 (1994); (F. D. Ledley et al., *Cell Biochem.* 18A:226 (1994)).

Another approach to targeted gene delivery is the use of molecular conjugates, which consist of protein or synthetic ligands to which a nucleic acid- or DNA-binding agent has been attached for the specific targeting of nucleic acids to cells (R. J. Cristiano et al., *Proc. Natl. Acad. Sci. USA* 90:11548-52 (1993); B. A. Bunnell et al., *Somat. Cell Mol. Genet.* 18:559-69 (1992); M. Cotten et al., *Proc. Natl. Acad. Sci. USA* 89:6094-98 (1992)). Once the DNA is coupled to the molecular conjugate, a protein-DNA complex results. This gene delivery system has been shown to be capable of targeted delivery to many cell types through the use of different ligands (R. J. Cristiano et al., *Proc. Natl. Acad. Sci. USA* 90:11548-52 (1993)). For example, the vitamin folate has been used as a ligand to promote delivery of plasmid DNA into cells that overexpress the folate receptor (e.g., ovarian carcinoma cells) (S. Gottschalk et al., *Gene Ther.* 1:185-91 (1994)). The malaria circumsporozoite protein has been used for the liver-specific delivery of genes under conditions in which ASOR receptor expression on hepatocytes is low, such as in cirrhosis, diabetes, and hepatocellular carcinoma (Z. Ding et al., *J. Biol. Chem.* 270:3667-76 (1995)). The overexpression of receptors for epidermal growth factor (EGF) on cancer cells has allowed for specific uptake of EGF/DNA complexes by lung cancer cells (R. Cristiano et al., *Cancer Gene Ther.* 3:4-10 (1996)). The presently preferred gene delivery method is lipofection.

In another aspect, the present invention provides methods of ameliorating the symptoms of a disease. The methods of this aspect of the invention include the steps of (1) introducing into the liver of a mammalian subject a vector comprising a nucleic acid expression cassette, said expression cassette comprising: (a) an hepatic locus control element; (b) an hepatic promoter located 3' to the hepatic locus control element; (c) a coding sequence located 3' to the hepatic promoter, said coding sequence encoding a polypeptide; (d) a polyadenylation signal located 3' to the coding sequence; (e) an intron located 3' to the hepatic promoter and 5' to the polyadenylation signal, wherein elements (a), (b), (c), (d) and (e) are operably linked to express the polypeptide encoded by the coding sequence; and (2) expressing a therapeutic amount of said polypeptide in the liver.

The vectors can be introduced into the liver by any art-recognized means, such as by direct injection into the liver, portal vein injection, tail vein injection, subcutaneous injection, and retroductal injection. The vectors of the present invention are useful in the practice of the methods of this aspect of the invention. Any polypeptide can be expressed in the liver in order to ameliorate the symptoms of one of more diseases. Representative examples of polypeptides that can be expressed in the liver are polypeptides involved in blood clotting. In some embodiments of the methods of the invention, the therapeutic amount of the polypeptide is expressed in the liver for a period in excess of 100 days, such as at least 200 days, at least 300 days, at least 400 days, or at least 500 days. The present invention also provides methods of expressing a polypeptide in the liver of a mammalian subject. The methods of this aspect of the invention include the same steps as the methods of the invention for ameliorating the symptoms of a disease, except that the amount of expressed polypeptide can be, but is not necessarily, sufficient to ameliorate the symptoms of a disease.

The following examples merely illustrate the best mode now contemplated for practicing the invention, but should not be construed to limit the invention. All literature citations herein are expressly incorporated by reference.

EXAMPLE 1

This example describes the materials and methods used in the experiments described in Example 2.

Construction of plasmids: Factor IX expression cassettes were first constructed in Bluescript vector backbones (pB-SKS). The plasmid pBS-hAAT-bpA (Long, G. L. et al., *Biochemistry* 23:4828-37 (1984)) was digested with EcoRI to remove the hAAT cDNA, and blunt ended. The human Factor IX cDNA (SEQ ID NO: 2) was cut out from pCMV-FIX (Armentano, D. et al., *Proc. Natl. Acad. Sci. USA* 87:6141-5 (1990)) using BamHI and KpnI, blunt ended, and then cloned into the blunt ended EcoRI site of pBS-bpA to yield pBS-FIX-bpA. Next, pBS-FIX-bpA was digested with SalI and blunt ended. The hAAT promoter (SEQ ID NO: 5) was obtained from digestion of pLTR-hAATp-FX (Le, M. et al. *Blood* 89:1254-9 (1997)) with BglII and NotI, and the ApoE-enhancer-hAAT- promoter fragment was obtained by digestion of pLTR-ApoE-enh-hAATp-hAAT (Hafenrichter, D. G. et al., *Blood* 84:3394-404 (1994)) with BglII. Both enhancer-promoter fragments were then blunt ended and inserted into the SalI-blunt ended site of pBS-FIX-bpA to generate pBS-hAATp-FIX-bpA and pBS-ApoE-enh-hAATp-FIX-bpA constructs. The plasmid pBS-hAATp-FIX-bpA was further digested with KpnI and ligated with a 711 bp KpnI fragment of ApoE-HCR amplified by PCR from plasmid pLIV7 (Dang, Q. et al., *J. Biol. Chem.* 270:22577-85 (1995)) to generate pBS-ApoE-HCR-hAATp-FIX-bpA. The Factor IX minigene (including Factor IX intron A (SEQ ID NO: 1) and 1.7 kb 3'-UTR (SEQ ID NO: 7)) was obtained from digestion of plasmid AVS17H9F.CM (Kaleko, M. et al., *J. Cell. Biochemistry* 21:A:366 (1995)) by SpeI and ClaI, and blunt-ended. pBS-FIX-bpA was digested with XhoI to release hFIX cDNA (SEQ ID NO: 2) and blunt-ended, and then ligated with the Factor IX minigene to give pBS-FIXmg-bpA. The FIXmg-bpA fragment was then cut out from pBS-FIXmg-bpA by CalI and SpeI. pBS-hAAT-FIX-bpA, pBS-ApoE-enh-hAAT-FIX-bpA, and pBS-ApoE- HCR-hAAT-FIX-bpA were digested with SpeI and ClaI to give three fragments from each plasmid, pBS, FIX-bpA, and three different enhancer-promoter-HCR combinations. The digested plasmid, pBS, was then ligated with FIXmg-bpA fragment and three different enhancer-promoter-HCR combinations to give three plasmids respectively, pBS-hAAT-FIXmg-bpA, pBS-ApoE-enh-hAAT-FIXmg-bpA, and pBS-ApoE-HCR-hAAT-FIXmg-bpA. The ApoEHCR fragments amplified by PCR were sequenced and all the constructs made were checked to ensure their correctness prior to their cloning into the expression plasmids.

The plasmid containing the retroviral vector backbone, pLX, was generated by deleting the neo gene from pLNCX (Miller, A. D., Hum Gene Ther 1:5-14 (1990)). The plasmid, pLX was then digested with HpaI. Various hFIX expression cassettes were cut out from the pBS constructs described above with SpeI, blunt-ended, and cloned into HpaI site of pLX to yield a series of LX-constructs listed in FIG. 2A.

Figure 2A:
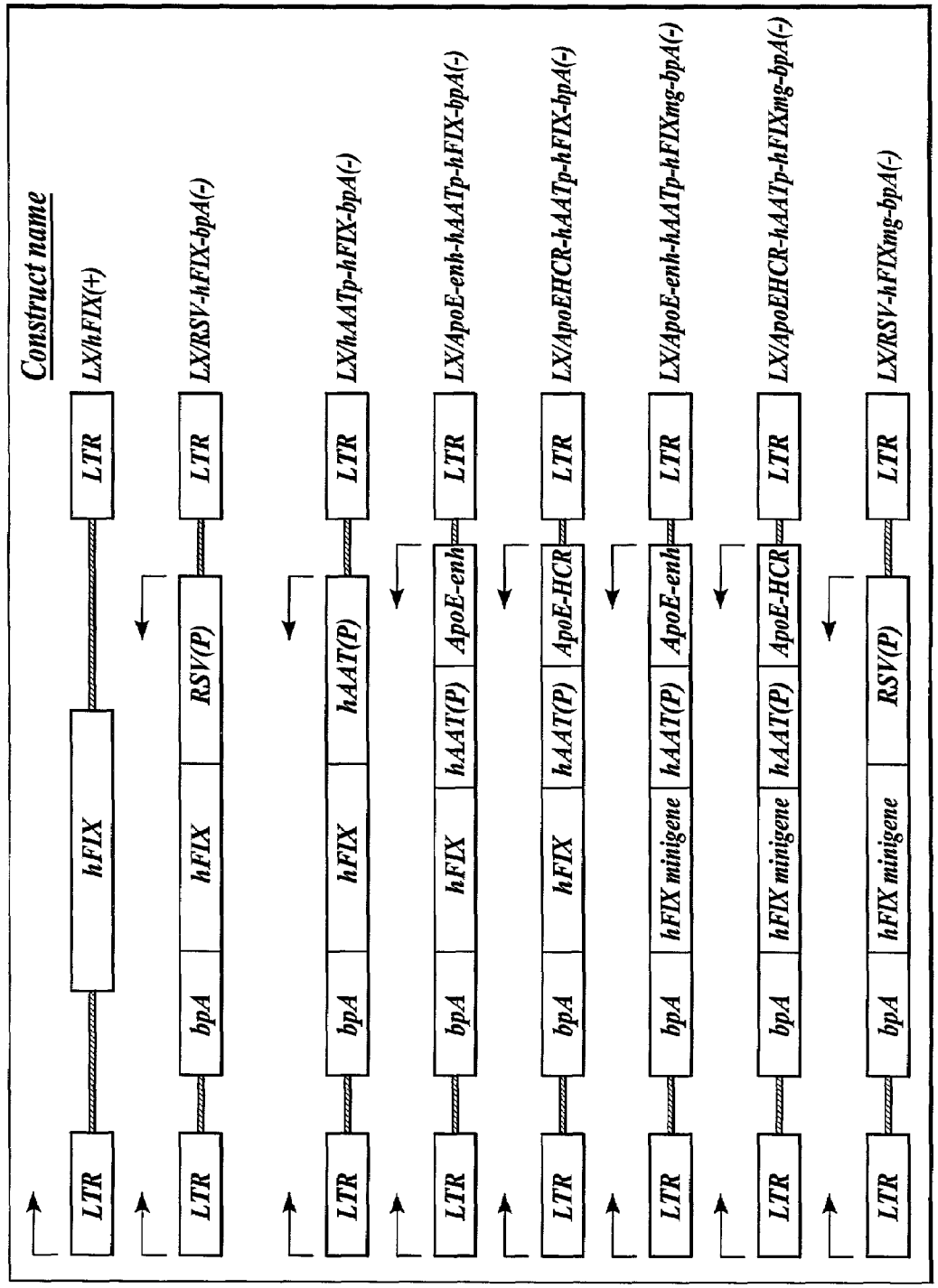
FIG. 2A shows retroviral constructs including different combinations of cis-acting regulatory elements for evaluation of Factor IX gene expression levels. (+) denotes the expression cassettes were inserted in the natural orientation to the transcription directed by 5'-LTR; (−) denotes the expression cassettes were inserted in the opposite orientation to the transcription directed by 5'-LTR; (P) indicates promoters, and (E) enhancers. hFIX minigene is composed of hFIX cDNA (SEQ ID NO: 2) plus 1.4 kb truncated intron A (SEQ ID NO: 1) plus 1.7 kb 3' UTR (SEQ ID NO: 7). Abbreviations used in FIGS. 2A and 2B are: LTR, long terminal repeats; hFIX, human Factor IX cDNA (1.4 kb) (SEQ ID NO: 2); hAAT (P), human α1-antitrypsin promoter (408 bp) (SEQ ID NO: 5); bpA, bovine growth hormone polyadenylation signal (SEQ ID NO: 6); ApoE, four copies of 154 bp ApoE enhancer sequence (SEQ ID NO: 8); ApoEHCR, hepatic locus control region from the ApoE gene locus (771 bp) (SEQ ID NO: 4); ApoEHCR(s), a shorter fragment of hepatic locus control region from the ApoE gene locus (SEQ ID NO: 9); RSV, Rous Sarcoma Virus-LTR promoter (400 bp); hFIXmg, a human factor minigene containing Factor IX cDNA (1.4 kb) (SEQ ID NO: 2), 1.4 kb truncated intron A (SEQ ID NO: 1), and 1.7 kb 3'-UTR (SEQ ID NO: 7).
Figure 2B:
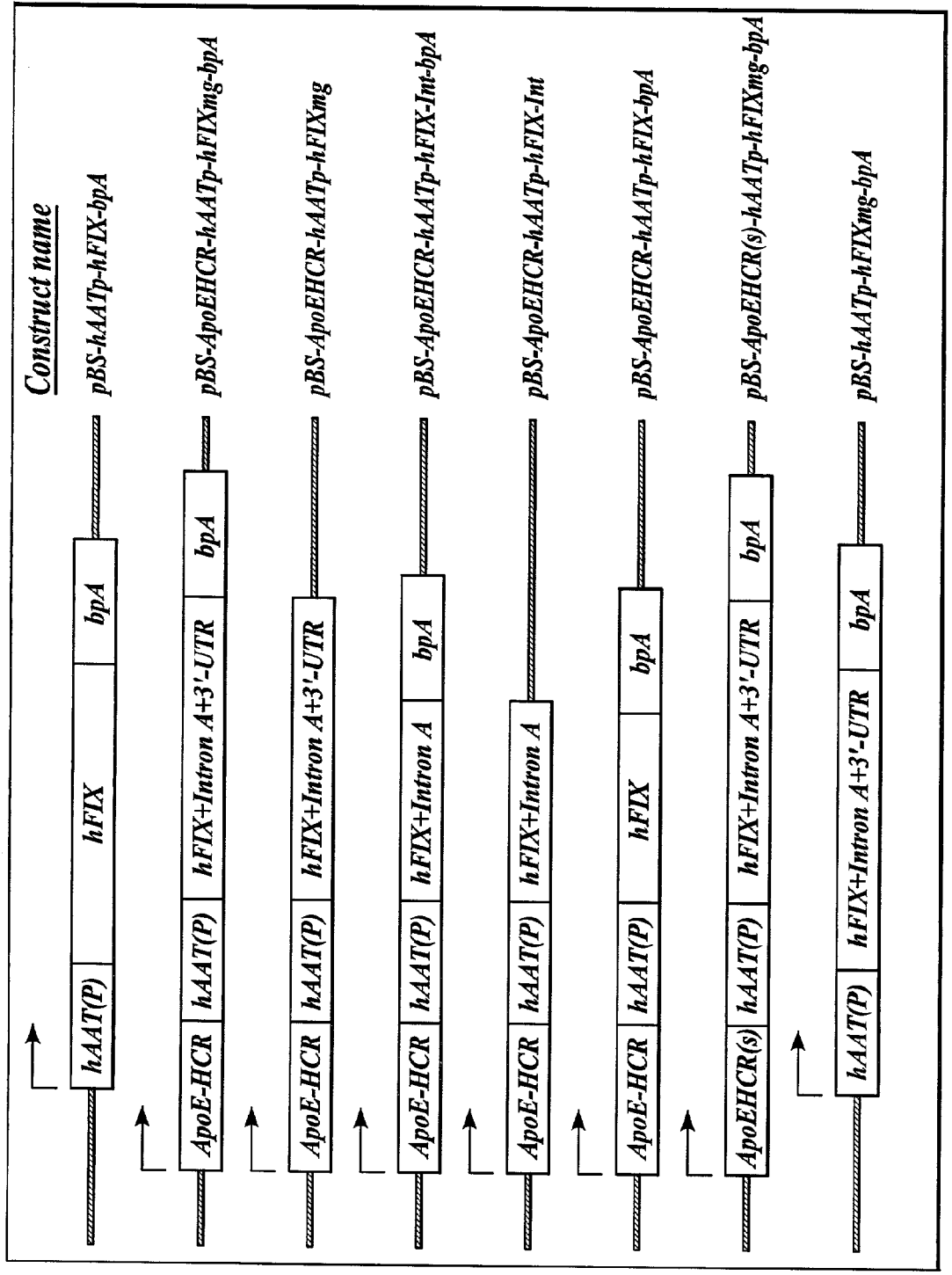
FIG. 2B shows bluescript plasmids including different combinations of cis-acting regulatory elements for evaluation of Factor IX gene expression levels.

For characterizing the essential elements for persistent Factor IX gene expression, more bluescript constructs were made for comparison with a total of eight plasmids in animal experiments (FIG. 2B). Either bpA (SEQ ID NO: 6) or Factor IX 3'-UTR (SEQ ID NO: 7) was deleted from plasmid pBS-ApoEHCR-hAATp-hFIXmg-bpA to make pBS-ApoE-HCR-hAATp-hFIXmg or pBS-ApoEHCR-hAATp-hFIX-Int-bpA. Next bpA (SEQ ID NO: 6) was deleted from pBS-ApoEHCR-hAATp-hFIX-Int-bpA to yield pBS-ApoE-HCR-hAATp-hFIX-Int. Plasmid pBS-hAATp-FIX-bpA was digested with KpnI and ligated with a shorter, 331 bp KpnI fragment of ApoE-HCR amplified by PCR from plasmid pLIV7 (Dang, Q. et al., J. Biol. Chem., 270:22577-85 (1995)) to generate pBS-ApoEHCR(s)-hAATp-FIX-bpA. The ApoEHCR(s)-hAATp or hAAT promoter fragment (SEQ ID NO: 5) was ligated with pBS-bpA and hFIX-mg fragments purified as described earlier to yield pBS-ApoE-HCR(s)-hAATp-hFIXmg-bpA or pBS-hAATp-hFIXmg-bpA. All the plasmid DNAs were prepared by alkaline lysis method and purified by Maxi-Prep kits from Qiagen. No protein or RNA was detectable in these preparations.

Cell culture and transfections: Mouse hepatoma cells (Hep1A) were cultured in Dulbecco's modified Eagle's medium supplemented with L-glutamine, antibiotics (penicillin and streptomycin), and 10% fetal calf serum. Human hepatoma cells (HepG2) were cultured in minimal Eagle's medium supplemented with L-glutamine, antibiotics, 1% nonessential amino acids, 1% sodium pyruvate, and 10% fetal calf serum. Nontransformed mouse hepatocyte cells (NMH) were cultured in 1:1 mixture of Dulbecco's modified Eagle's and Ham's F-12 medium supplemented with 5 µg/ml insulin, 5 µg/ml transferrin, 5 ng/ml selenium, 0.1 mM dexamethasone, 0.1% gentamycin, 10 mM nicotinamide, and 20 ng/ml epidermal growth factor. All three cell lines were maintained in a 5% $CO_2$ atmosphere at 37° C.

Plasmid DNA (2 µg) and pBS-RSV-hAAT-bpA (1 µg) used as an internal control were cotransfected into cultured cells by Lipofectamine reagents (Life Technologies). Each transfection was repeated at least three times. Sixty hours after transfection, cell culture media were collected and analyzed for total human α1-antitrypsin or Factor IX antigen (Kay, M. A. et al., Proc. Natl. Acad. Sci. USA 91:2353-7 (1994)) by an ELISA assay using polyclonal antisera to α1-antitrypsin or hFIX (Bray, G. L. et al., J. Lab. Clin. Med. 107:269-78 (1986)), respectively.

Direct injection of plasmids into portal vein of mice: C57B1/6 mice were obtained from Jackson Laboratory and housed under SPF conditions. Animals were treated according to the NIH guidelines for animal care at the University of Washington and Stanford University. The method was similar to that described by Budker et al. (Budker, V. et al., Gene Therapy 3:593-9 (1996)) and resulted in a small percentage of transfected hepatocytes. The mice were injected with 100 µg of the plasmid DNA in a hypertonic solution (containing 0.9% saline, 15% mannitol (Sigma) and 3.5 units/ml of heparin to prevent microvascular thrombosis) over 30 seconds (s) through the portal vein. In order to temporarily occlude the hepatic veins during the injection, a 5 mm, Kleinert-Kutz microvessel clip (Edward Weck) was applied at the junction of the hepatic vein and vena cava. Mice were periodically bled by the retro-orbital technique. The human Factor IX level in the mouse plasma was determined as total hFIX antigen by an ELISA assay using polyclonal antisera to hFIX.

Direct injection of plasmids into tail vein of mice: C57B1/6 mice (Taconic) were housed under SPF conditions at Stanford University and the University of Washington. The method was similar to that described by Liu et al. (Liu, F. et al. Gene Ther. 6:1258-1266 (1999)) and Zhang et al. (Zhang, G. et al., Human Gene Ther. 10:1735-1737 (1999)). Twenty microgram of the respective plasmid for testing along with 5 µg of a control plasmid (pBS-RSV-hAAT-bpA) in 2 ml 0.9% saline solution were injected into the tail vein of a mouse over 6-8 seconds. This method has been shown to transfect about 40% of the hepatocytes. The mice were bled periodically in order to evaluate hFIX or α1-antitrypsin levels in the plasma by ELISA as described above.

EXAMPLE 2

This example describes the expression of Factor IX obtained by introducing the plasmids described in Example 1 into mouse liver cells.

Design of vector constructions: In order to optimize production of human Factor IX (FIX) in hepatocytes, gene expression was investigated by incorporating various combinations of cis-acting regulatory sequences including a tissue-specific promoter-enhancer, hepatic locus control region (SEQ ID NO: 4), intron A (SEQ ID NO: 1), and 3'-untranslated region (SEQ ID NO: 7) into retroviral-containing plasmid DNAs.

A simple retroviral backbone containing the human Factor IX cDNA (SEQ ID NO: 2) was first utilized. For hepatic gene transfer, a liver-specific promoter (SEQ ID NO: 5) from the α1-antitrypsin gene was added, with or without four copies of the ApoE-enhancer (SEQ ID NO: 8) (Shachter, N. S. et al., J. Lipid Res. 34:1699-707 (1993)). The α1-antitrypsin promoter (SEQ ID NO: 5) was selected because it is a strong liver-specific promoter (Hafenrichter, D. G. et al., Blood 84:3394-404 (1994), and its function is not inhibited by the LTR promoter in the retroviral vector (Wu, X., et al., Hum. Gene Ther. 7:159-71 (1996)). Furthermore, it was reported that by adding four copies of the strong 154 bp liver-specific apolipoprotein E (ApoE) enhancer (SEQ ID NO: 8) (Shachter, N. S. et al., J. Lipid Res. 34:1699-707 (1993)) upstream of the hAAT promoter (SEQ ID NO: 5), expression of the α1-antitrypsin gene was further increased more than 15-fold over the constructs having other promoter-enhancers (Okuyama, T. et al., Hum. Gene Ther. 7:637-45 (1996)).

To overcome the possible silencing effect by the position of integration, a recently reported locus control region (LCR) (SEQ ID NO: 4) for the liver-specific expression of the ApoE gene, ApoE-HCR (Simonet, W. S. et al., J. Biol. Chem. 268:8221-9) was incorporated into some of the expression cassettes. This hepatic control region (SEQ ID NO: 4) is located in the ApoE/CI/CII locus and localized to a 319 bp region for full functional LCR activities. This element confers copy-number dependent, position independent gene expression, and was shown to exhibit 10 fold higher activity than the ApoE enhancer (SEQ ID NO: 8) in a transgenic mouse model (Dang, Q. et al., *J. Biol. Chem.* 270:22577-85 (1995)). Since it is not clear how a multimerized LCR would affect gene transcription in vivo, a single ApoE-HCR sequence (SEQ ID NO: 4) was used in the plasmid expression cassettes. RSV and LTR promoters were used as controls.

Retroviral vector containing plasmids were constructed to compare the strength of these cis-elements systematically (FIG. 2A). The control viral LTR (LX/hFIX) and RSV (LX/RSV-hFIX-bpA(-)) promoters were used and the following liver-specific elements were incorporated; the hAAT promoter (SEQ ID NO: 5) alone, or with the addition of an ApoE-enhancer (SEQ ID NO: 8), or ApoE-HCR (SEQ ID NO: 4) (LX/hAAT-hFIX-bpA(-), and LX/ApoE-enh-hAAT-hFIX-bpA(-), LX/ApoE-HCR-hAAT-hFIX-bpA(-), FIG. 2A). The expression cassettes with added internal promoters were inserted in an opposite transcriptional orientation relative to the LTR promoter to avoid promoter interference with the viral LTR promoter in vivo (Emerman, M., and Temin, H. M., *Mol. Cell Biol.* 6:792-800 (1986); Ghattas, I. R. et al., *Mol. Cell Biol.* 11:5848-59 (1991)), and for comparison with the constructs containing the incorporation of an intron (SEQ ID NO: 1) and 3'-UTR (SEQ ID NO: 7). Additionally, an exogenous polyadenylation signal (SEQ ID NO: 6) was added to the 3' end of the Factor IX cDNA to ensure proper processing of the mRNA. The goal was to compare the relative strength of the Moloney LTR and an internal RSV-LTR with the different liver promoters discussed above.

Next the hFIX minigene composed of the hFIX cDNA (SEQ ID NO: 2), 1.4 kb truncated intron A (SEQ ID NO: 1), and 1.7 kb 3'-UTR (SEQ ID NO: 7) was incorporated with different combinations of the promoter-enhancer sequences. These expression cassettes were inserted in the opposite transcriptional orientation to that of the retroviral LTR (LX/ApoE-enh-hAAT-hFIXmg-bpA(-), LX/ApoE-HCR-hAAT-hFIXmg-bpA(-), and LX/RSV-hIFIXmg-bpA(-), FIG. 2A). This was done to ensure that splicing of the Factor IX intron (SEQ ID NO: 1) and the polyadenylation signal in the 3'-UTR (SEQ ID NO: 7) would not interfere with the production of full length viral transcripts in packaging cell lines if these plasmids were used to make retroviral vectors.

In vitro testing of gene expression in cell culture systems: These plasmids were first tested in three hepatic cell culture systems for the following two reasons. First, to confirm construct functionality prior to in vivo studies. Second, to establish a baseline for comparison and predictability with in vivo studies.

Figure 3A:
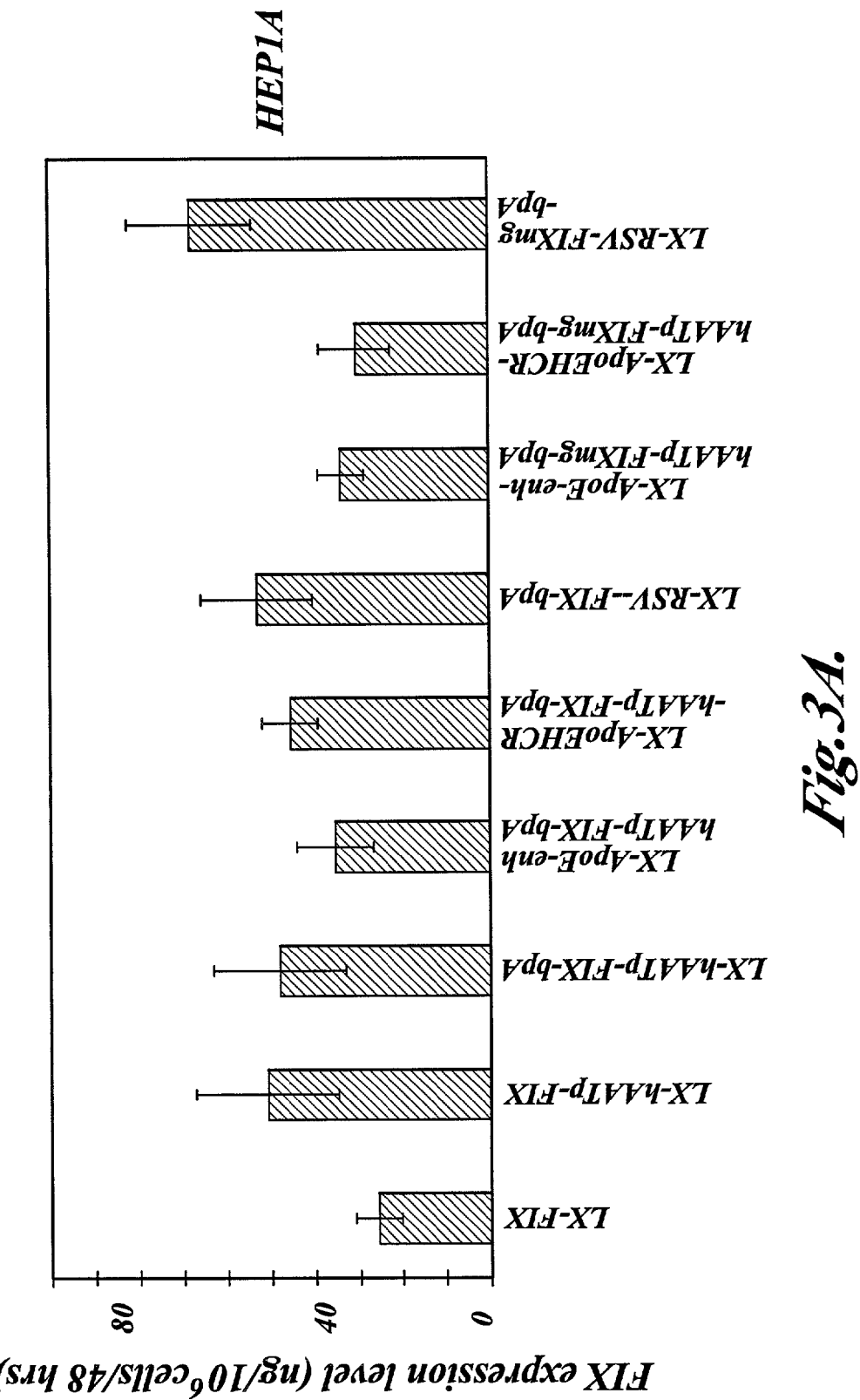
FIG. 3A shows the results of experiments to evaluate promoter strength in a cell culture system. Different plasmid constructs were transiently transfected into hepatic cell line Hep1A. Culture media were collected two days after transfection and analyzed for human Factor IX and α1-antitrypsin levels by ELISA. Each transfection was repeated at least three times. Factor IX expression levels were then normalized against α1-antitrypsin expression levels produced by a control pBS-RSV-hAAT-bpA plasmid.
Figure 3B:
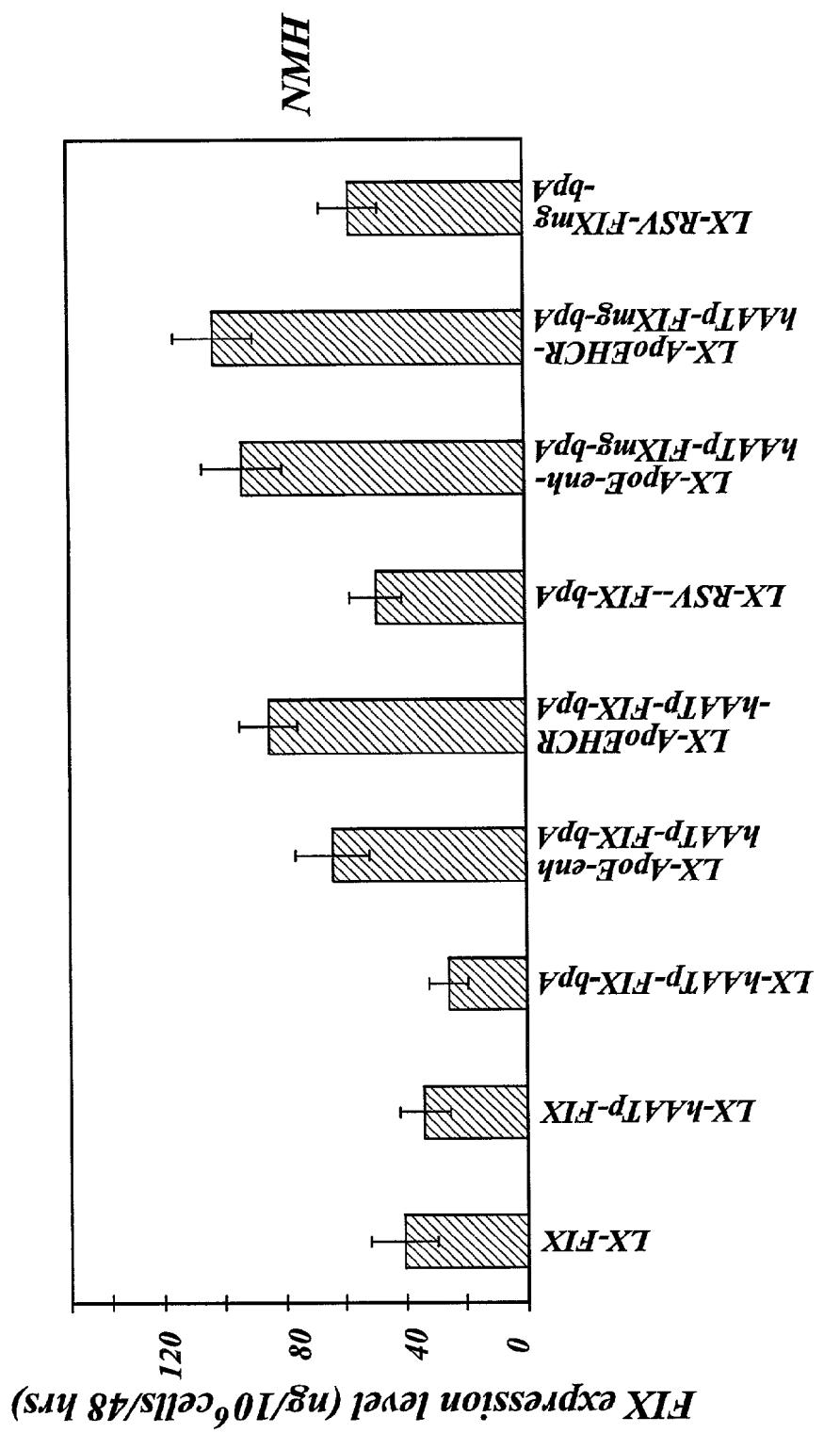
FIG. 3B shows the results of experiments to evaluate promoter strength in a cell culture system. Different plasmid constructs were transiently transfected into hepatic cell line NMH. Culture media were collected two days after transfection and analyzed for human Factor IX and α1-antitrypsin levels by ELISA. Each transfection was repeated at least three times. Factor IX expression levels were then normalized against α1-antitrypsin expression levels produced by a control pBS-RSV-hAAT-bpA plasmid.
Figure 3C:
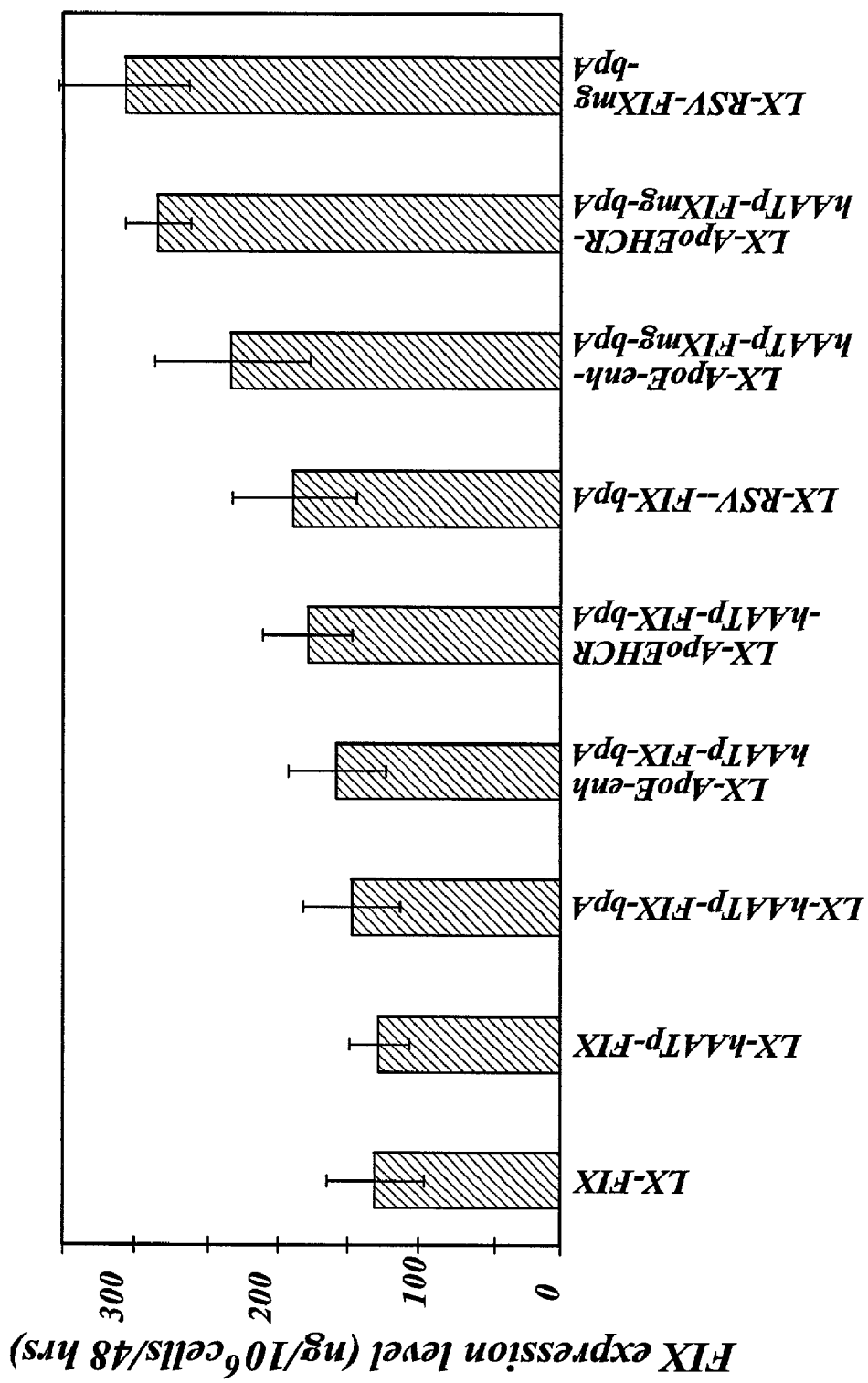
FIG. 3C shows the results of experiments to evaluate promoter strength in a cell culture system. Different plasmid constructs were transiently transfected into hepatic cell line HepG2. Culture media were collected two days after transfection and analyzed for human Factor IX and α1-antitrypsin levels by ELISA. Each transfection was repeated at least three times. Factor IX expression levels were then normalized against α1-antitrypsin expression levels produced by a control pBS-RSV-hAAT-bpA plasmid.

Two days after transfection in cell culture, the culture media were collected and analyzed by ELISA assay. Factor IX expression levels were normalized by the human alpha 1-antitrypsin levels (HAAT) expressed from a cotransfected control pBS-RSV-hAAT-bpA plasmid. In Hep1A cells, low level Factor IX expression was observed with all the constructs with 1-2.5 fold variance (FIG. 3). Interestingly, the RSV-LTR promoter was just as active as the liver-specific enhancer-promoters. The presence of the intron (SEQ ID NO: 1) and 3'-UTR region (SEQ ID NO: 7) had little effect on gene expression.

Next these plasmids were tested in a nontransformed hepatocyte (NMH) cell line derived from mice transgenic for transforming growth factor alpha (Wu, J. C. et al., *Proc Natl. Acad. Sci USA* 91:674-8), which may have properties more closely related to in vivo conditions. In general, a higher level of Factor IX expression was achieved in the NMH cells than those obtained in Hep1A cells (FIG. 3) with all of the tested plasmids. The Factor IX level was about two-fold higher with either the addition of an ApoE-enhancer (SEQ ID NO: 8) or ApoE-HCR (SEQ ID NO: 4) compared with the hAAT promoter (SEQ ID NO: 5) alone.

Lastly, these plasmids were tested in HepG2 cells, which is a human hepatoma cell line. Since all the liver-specific regulatory cis-sequences used were derived from human sequences, these elements may only be fully functional in human hepatocytes. As shown in FIG. 3, the Factor IX cDNA (SEQ ID NO: 2) directed by hepatocyte-specific enhancer-promoters in the vector was expressed in higher levels than those in the other two mouse cell lines. However, the RSV promoter was also more active and had similar strength as the liver-specific enhancer-promoters in HepG2 cells. The inclusion of the hFIX intron (SEQ ID NO: 1) and 3'-UTR (SEQ ID NO: 7) in the vector increased the gene expression level by ~1.5 fold.

In vivo direct plasmid injection via portal vein: The expression of the plasmid DNAs was studied in vivo by the direct injection of plasmids into the portal vein (Budker, V. et al., *Gene Ther.* 3:593-8 (1996)). 100 µg of the respective retroviral plasmid in hypertonic solution was delivered intraportally into C57Bl/6 mouse whose hepatic vein was transiently occluded. Half of the mice died during surgery or one day after surgery. All the remaining mice survived up to 40 days (the duration of the experiment).

Figure 4A:
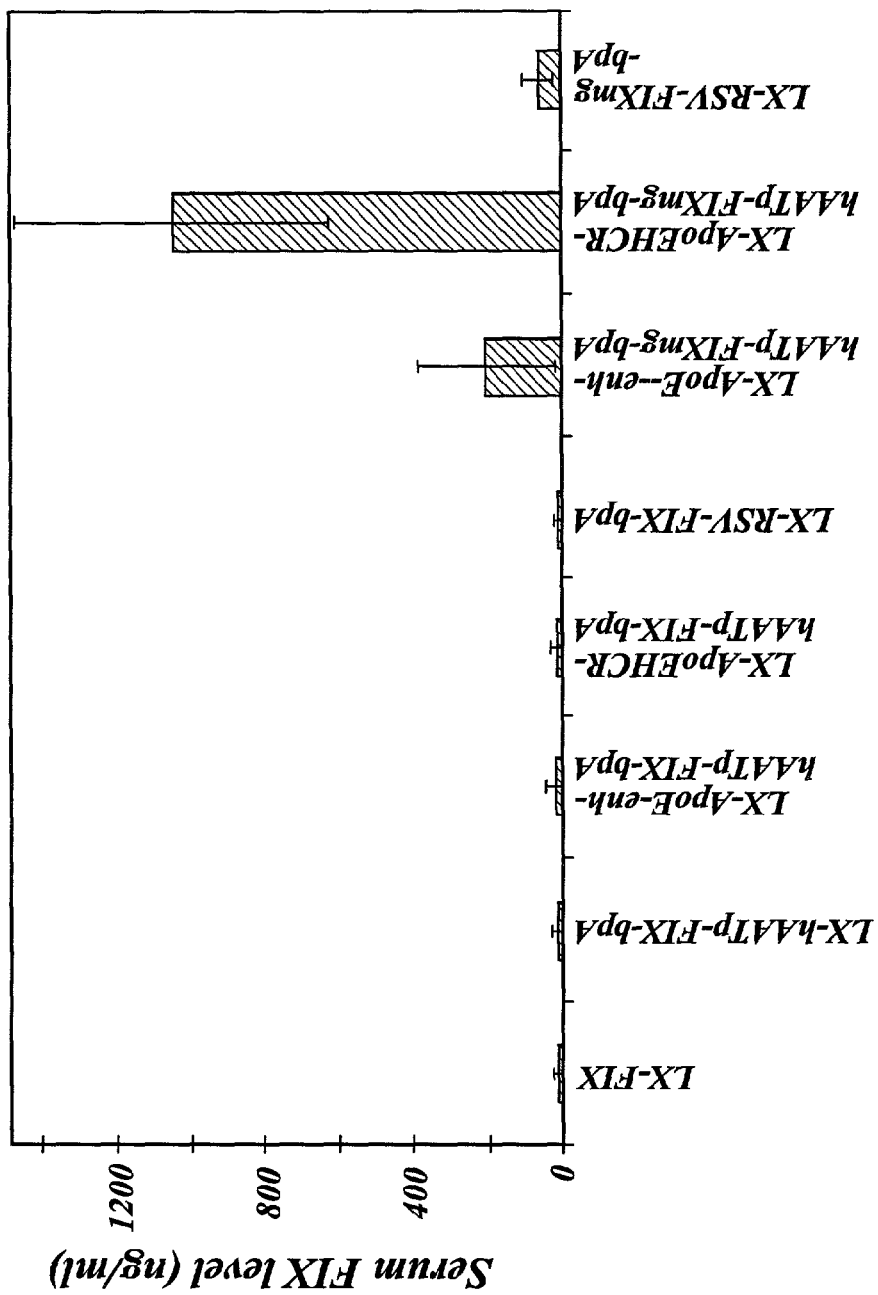
FIG. 4A shows Factor IX gene expression after direct injection of plasmids, each containing an expression cassette of the invention, into the portal vein of mice. 100 μg of the respective plasmid was delivered intraportally into C57/BL6 mouse (n=6 per group; about half of the animals did not survive the procedure) whose hepatic vein was transiently occluded. Two days after infusion, the serum was analyzed for human Factor IX levels by ELISA.

Two days after plasmid injection, collected plasma samples were analyzed for hFIX protein by ELISA. As shown in FIG. 4A, animals infused with LX-FIX(+) without internal promoters gave a basal serum level of 5 -10 ng/ml FIX. The addition of an added internal hAAT promoter (SEQ ID NO: 5), ApoE-enh (SEQ ID NO: 8)-hAAT-promoter (SEQ ID NO: 5), ApoE-HCR (SEQ ID NO: 4)-hAAT-promoter (SEQ ID NO: 5), or RSV promoter, did not augment Factor IX expression from constructs containing the Factor IX cDNA (SEQ ID NO: 2) (LX-hAAT-hFIX-bpA, LX-ApoE-enh-hAAT-hFIX-bpA, LX-ApoE-HCR-hAAT-hFIX-bpA, and LX-RSV-hFIX-bpA). However, in mice injected with the construct containing RSV promoter element and a human Factor IX minigene sequence (LX-RSV-FIXmg-bpA), Factor IX levels were 3-fold higher than those obtained from constructs containing the hFIX cDNA (SEQ ID NO: 2). In mice injected with the construct containing 154 bp ApoE-enhancer element (SEQ ID NO: 8) and hAAT promoter (SEQ ID NO: 5) in combination with a hFIX minigene sequence (LX-ApoE-enh-hAAT-FIXmg-bpA), Factor IX levels were about ten fold higher (50-180 ng/ml) than those obtained from constructs with hFIX cDNA (SEQ ID NO: 2). Most interestingly, when the ApoE-HCR element (SEQ ID NO: 4) and hAAT-promoter (SEQ ID NO: 5) were used in combination with the FIX minigene sequence (LX-ApoE-HCR-hAAT-FIXmg-bpA), Factor IX levels were ~67 fold higher (0.7-1.5 µg/ml) than the basal level obtained from animals receiving the LX-FIX construct. This level of Factor IX expression, ~30% of the normal plasma Factor IX concentration (5 µg/ml), was in a concentration that would be curative for individuals with hemophilia B.

Figure 4B:
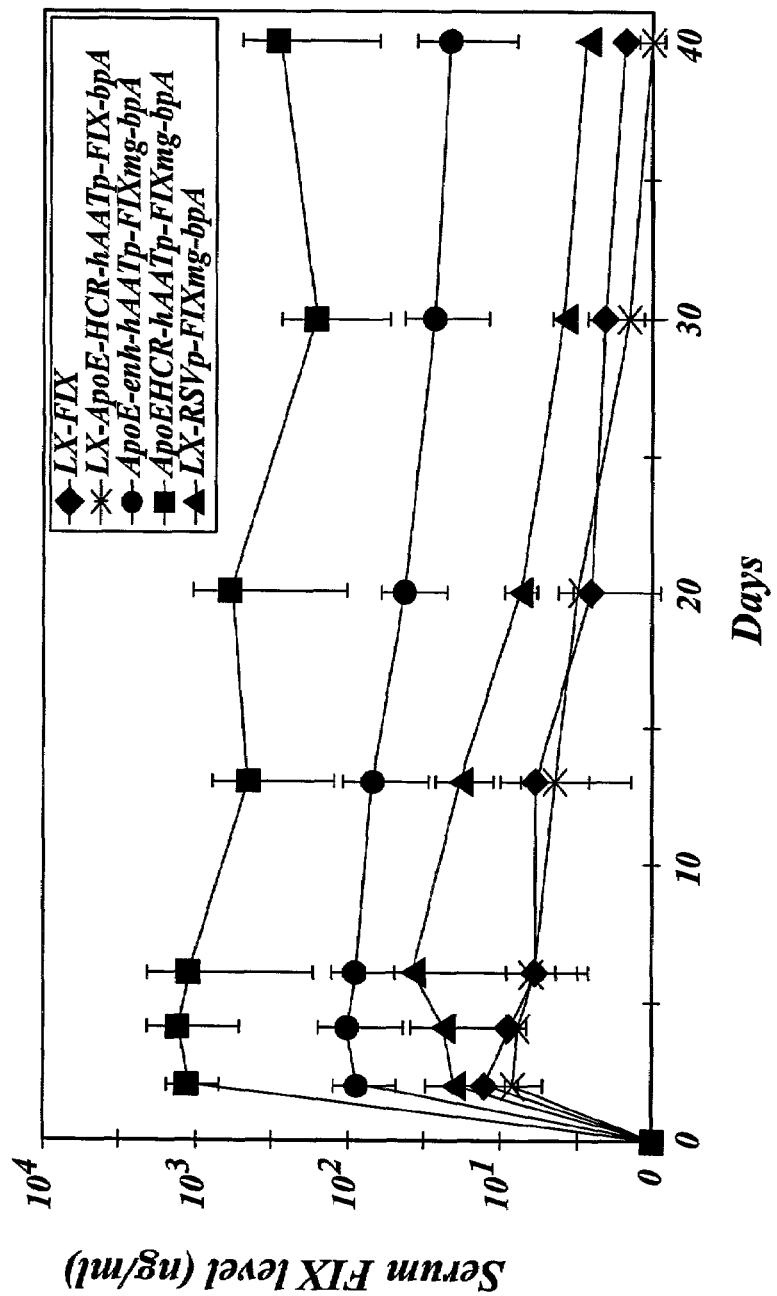
FIG. 4B shows Factor IX serum levels over time in the injected mice described in the legend to FIG. 4A. Different symbols represent expression levels from mice injected with different plasmids: diamond, LX-FIX(+); asterisk, LX-ApoE-HCR-hAATp-FIX-bpA(−); circle, LX-ApoE-enh-hAAT-FIXmg-bpA(−); square, LX-ApoE-HCR-hAAT-FIXmg-bpA(−); triangle, LX-RSVp-FIXmg-bpA(−).

To test how long plasmid-mediated gene expression persisted in the mice, plasma samples were periodically analyzed for hFIX. In mice injected with constructs containing the Factor IX cDNA (SEQ ID NO: 2), Factor IX levels dropped to undetectable level 3 to 7 days post vector infusion. In mice injected with constructs containing the human Factor IX minigene, Factor IX levels were initially higher and persisted longer, yet the protein levels fell slowly over time (FIG. 4B). The Factor IX concentrations from the highest producing mouse injected with construct LX-ApoE-HCR-hAAT-FIXmg-bpA persisted at high levels for a week and slowly decreased to 200 ng/ml at 40 days after vector administration. The decline in gene expression was not unexpected because of the episomal nature of the plasmid in cells.

Figure 5:
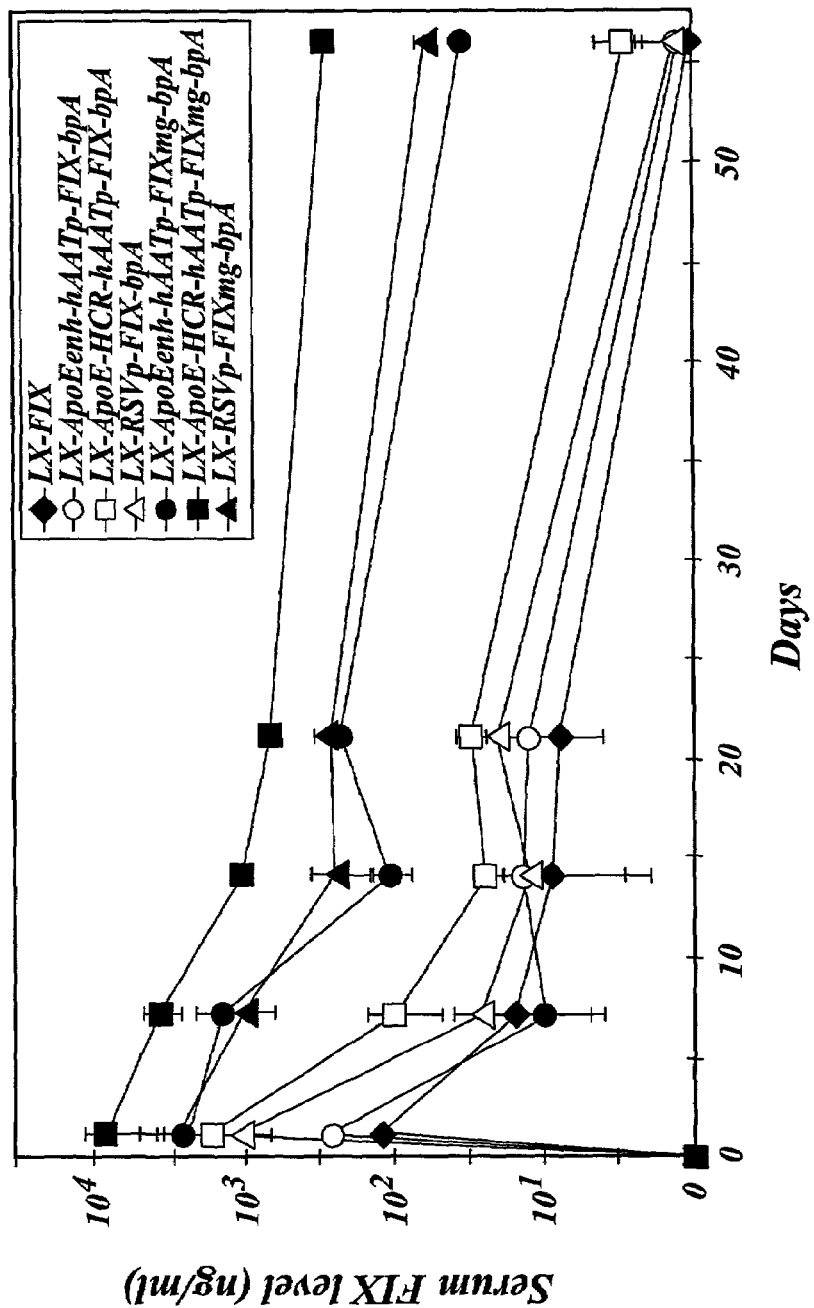
FIG. 5 shows plasma human Factor IX levels at various time points after direct injection of plasmids into the tail vein of mice. Twenty micrograms of the respective retroviral plasmid along with 5 μg of a control pBS-RSV-hAAT-bpA plasmid in 2 ml 0.9% saline solution were injected into the tail vein of C57/BL6 mouse (n=6 per group) over 6-8 seconds. Plasma was analyzed for human Factor IX and α1-antitrypsin levels by ELISA at different time points. Human Factor IX levels were then normalized against α1-antitrypsin expression levels for plasmid delivery efficiencies. Different symbols represent expression levels from mice injected with different plasmids: filled diamond, LX-FIX(+); open circle, LX-ApoE-enh-hAATp-FIX-bpA(−); open square, LX-ApoE-HCR-hAATp-FIX-bpA(−); open triangle, LX-RSVp-FIX-bpA(−); filled circle, LX-ApoEenh-hAATp-FIXmg-bpA(−); filled square, LX-ApoEHCR-hAATp-FIXmg-bpA(−); filled triangle, LX-RSVp-FIXmg-bpA(−).

Direct plasmid injection via tail vein. Due to the labor intensive nature of the surgical procedures for direct plasmid injection via portal vein as described above, another in vivo gene transfer method was used for testing the expression of these constructs in the liver. Twenty micrograms of the plasmid to be tested and 5 µg of a control pBS-RSV-hAAT-bpA plasmid were injected into the tail vein of mice. Previous studies showed that this method transfected about 40% of hepatocytes in vivo (Liu, F. et al., *Gene Ther.* 6:1258-1266 (1999); Zhang, G. et al., *Human Gene Ther.* 10:1735-1737 (1999)). The control plasmid was used to normalize for variations in plasmid injection procedures. Factor IX levels were highest one day after injection, but fell to lower or undetectable levels over time (FIG. 5). Although the absolute level of Factor IX gene expression levels were higher in tail versus portal vein infusions, the relative ratio of expression obtained from each construct relative to the basal expression level from the LX-FIX construct were comparable with those in the portal vein experiments (Table I).

Figure 6A:
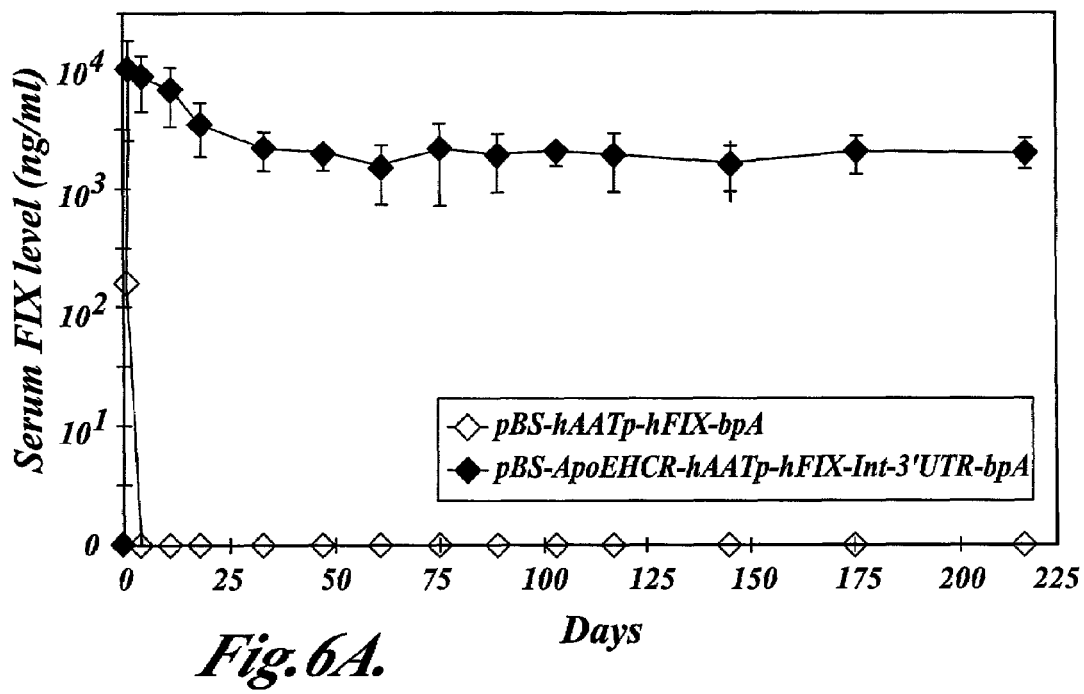
FIG. 6A shows human Factor IX gene expression levels after direct injection of various bluescript plasmids into the tail vein of mice. Twenty micrograms of the respective bluescript in 2 ml 0.9% saline solution were injected into the tail vein of C57B1/6 mouse (n=6 per group) over 6-8 seconds. Plasma was analyzed for human Factor IX levels by ELISA at different time points. Long term gene expression of human Factor IX levels were monitored after direct injection of the bluescript plasmids pBS-ApoE-HCR-hAATp-hFIX-Int-3'-UTR-bpA (filled diamond) or pBS-hAATp-hFIX-bpA (open diamond).
Figure 6B:
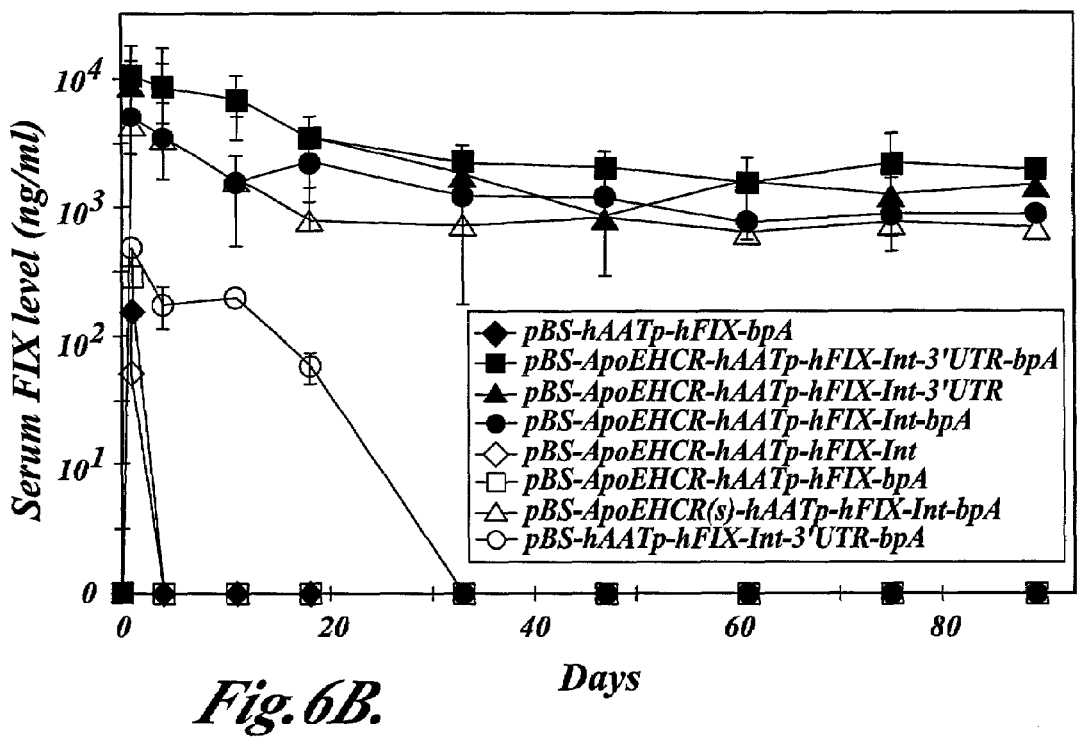
FIG. 6B shows the results of identifying elements required for persistent hFIX gene expression by testing different plasmids injected into the tail vein of mice. Twenty micrograms of the respective bluescript in 2 ml 0.9% saline solution were injected into the tail vein of C57B1/6 mouse (n=6 per group) over 6-8 seconds. Plasma was analyzed for human Factor IX levels by ELISA at different time points. Different symbols represent expression levels from mice injected with different plasmids: filled diamond, pBS-hAATp-hFIX-bpA; filled square, pBS-ApoEHCR-hAATp-hFIX-Int-3'UTR-bpA; filled triangle, pBS-ApoEHCR-hAATp-hFIX-Int-3'UTR; filled circle; pBS-ApoEHCR-hAATp-hFIX-Int-bpA; open diamond, pBS-ApoEHCR-hAATp-hFIX-Int; open square, pBS-ApoEHCR-hAATp-hFIX-bpA; open triangle, pBS-ApoEHCR(s)-hAATp-hFIX-Int-bpA; open circle, pBS-hAATp-hFIX-Int-3'UTR-bpA.

(Liu, F. et al., *Gene Ther.* 6:1258-1266 (1999); Zhang, G. et al., *Human Gene Ther.* 10:1735-1737 (1999)). An average of 10 µg/ml (two times the normal human level) was achieved one day after injection that slowly decreased to lower levels (FIG. 6A). However, the plasma concentrations stabilized at 7-8 weeks after injection in the range from 0.5 to 2 µg/ml and were maintained over 30 weeks (duration of the experiments). This concentration of hFIX was in the therapeutic range for treating hemophilia B. In order to begin to systematically delineate the critical element(s) required for persistent transgene expression, seven additional plasmids with a bluescript vector backbone were constructed (FIG. 2B) and injected into seven groups of mice (n=6/group). As shown in FIG. 6B, plasmids containing no intron sequence (SEQ ID NO: 1) (pBS-hAATp-hFIX-bpA, pBS-ApoEHCR-hAATp-hFIX-bpA) or no polyadenylation signal (pBS-ApoEHCR-hAATp-hFIX-Int) resulted in low to undetectable levels and transient gene expression. On the other hand, plasmids containing the combination of ApoE-HCR (SEQ ID NO: 4) and hAAT promoter (SEQ ID NO: 5), an intron (SEQ ID NO: 1) and polyadenylation signal(s) whether from 1.7 kb 3'-UTR (SEQ ID NO: 7) (pBS-ApoEHCR-hAATp-hFIXmg) or 0.3 kb bpA (SEQ ID NO: 6) (pBS-ApoEHCR-hAATp-hFIX-Int-bpA) or both (pBS-ApoEHCR-hAATp-hFIXmg-bpA), produced persistent, therapeutic levels (0.5-2 µg/ml) of hFIX. The plasmids containing 3'-UTR (SEQ ID NO: 7) gave ~2 fold higher expression than the one containing bpA (SEQ ID NO: 6) alone. Furthermore, the

TABLE I

COMPARISON OF FACTOR IX EXPRESSION LEVELS FROM CONSTRUCTS OBTAINED FROM IN VIVO AND IN VITRO EXPERIMENTS.

| Constructs | In vitro | | | In vivo | |
|---|---|---|---|---|---|
| | Hep1A | NMH | HepG2 | Portal vein | Tail vein |
| LX-FIX | 1.0 ± 0.21 | 1.0 ± 0.26 | 1.0 ± 0.26 | 1.0 ± 0.75 | 1.0 ± 0.18 |
| LX-hAAT-FIX | 2.0 ± 0.64 | 0.8 ± 0.20 | 1.0 ± 0.16 | — | — |
| LX-hAAT-FIX-bpA | 1.9 ± 0.59 | 0.6 ± 0.16 | 1.1 ± 0.26 | 1.3 ± 0.91 | — |
| LX-ApoE-hAAT-FIX-bpA | 1.4 ± 0.35 | 1.6 ± 0.29 | 1.2 ± 0.27 | 1.6 ± 1.84 | 2.2 ± 0.47 |
| LX-ApoE-HCR-hAAT-FIX-bpA | 1.8 ± 0.24 | 2.1 ± 0.24 | 1.4 ± 0.24 | 1.2 ± 1.38 | 14.0 ± 4.42 |
| LX-RSV-FIX-bpA | 2.1 ± 0.49 | 1.2 ± 0.21 | 1.4 ± 0.34 | 1.2 ± 0.92 | 8.8 ± 3.00 |
| LX-ApoE-hAAT-FIXmg-bpA | 1.3 ± 0.54 | 2.3 ± 0.32 | 1.8 ± 0.42 | 13.2 ± 11.4 | 21.3 ± 8.62 |
| LX-ApoE-HCR-hAAT-FIXmg-bpA | 1.2 ± 0.32 | 2.5 ± 0.32 | 2.2 ± 0.18 | 66.2 ± 26.6 | 68.9 ± 27.5 |
| LX-RSV-FIXmg-bpA | 2.7 ± 0.55 | 1.4 ± 0.24 | 2.3 ± 0.35 | 4.6 ± 2.63 | 22.8 ± 8.25 |

The expression level from the highest producing mouse was achieved from injection of construct LX-ApoE-HCR-hAAT-hFIXmg-bpA. This level was 69 fold higher than that of the LX-FIX construct, similar to that observed from the portal vein experiments. Taken together as a whole, the results obtained from in vivo studies were strikingly different from those obtained from the cell culture experiments. Interestingly, at 8 weeks of age, mice injected with constructs containing an intron (SEQ ID NO: 1) and 3'-UTR (SEQ ID NO: 7) sequences still produced low levels of FIX, whereas mice infused with the other plasmids did not.

The results above suggested that some of the cis DNA elements may have been responsible for differences in the persistence in gene expression. Systematic studies were undertaken to attempt to determine which elements were responsible for this finding. In order to avoid the influence from retroviral LTR sequences, the highest expressing cassette, ApoE-HCR-hAATp-hFIXmg-bpA, was cloned into a bluescript vector and 20 µg of the resulting plasmid in 2 ml of saline solution was injected into the tail vein of six mice plasmid pBS-hAATp-hFIXmg-bpA without an ApoE-HCR sequence (SEQ ID NO: 4) produced a lower level of initial gene expression, and the level dropped to undetectable four and a half weeks after plasmid injection, indicating ApoE-HCR (SEQ ID NO: 4) is an important element for persistent hFIX gene expression in these experiments. In addition, by replacing the 771 bp ApoE-HCR (SEQ ID NO: 4) with a shorter 328 bp ApoE-HCR (SEQ ID NO: 9) in plasmid pBS-ApoEHCR(s)-hAATp-hFIXmg-bpA, hFIX gene expression level stayed the same after plasmid injection. This demonstrates that the 328 bp ApoE-HCR fragment (SEQ ID NO: 9) containing the full functional LCR activities, is sufficient for augmenting the hFIX gene expression, consistent with results from transgenic mice experiments (Dang, Q. et al., *J. Biol. Chem.* 270:22577-85 (1995)). Taken together, these data showed that the inclusion of an intron and one polyadenylation signal increased and prolonged transgene expression in a plasmid after direct injection, and in combination with a locus control region (ApoE-HCR)

(SEQ ID NO: 4 or SEQ ID NO: 9) resulted in persistent as well as therapeutic levels of hFIX gene expression.

The best expressing plasmid tested in the in vivo study, LX-ApoE-HCR-hAAT-FIXmg-bpA, produced a maximal Factor IX level of 18 µg/ml one day after direct plasmid infusion. This level of Factor IX expression, is 3.6 fold above the normal plasma Factor IX concentration (5 µg/ml), and therefore in great excess of a curative level needed for treating hemophilia. Even over long periods of time, hFIX serum levels remained therapeutic at levels that were 10 to 40% of normal.

EXAMPLE 3

This example describes the materials and methods used in the experiments described in Example 4.

Figure 7A:
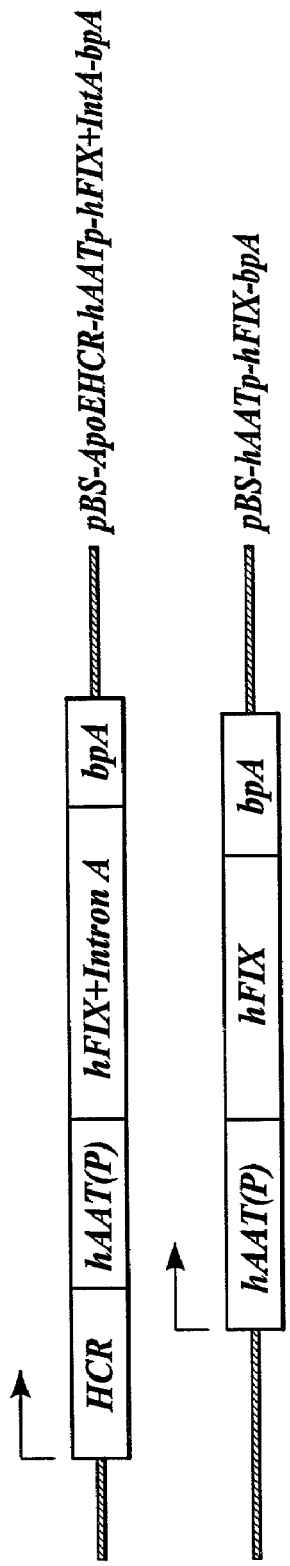
FIG. 7A shows the structure of constructs containing different hFIX expression cassettes. Abbreviations are: HCR, hepatic locus control region from ApoE gene locus (771 bp) (SEQ ID NO: 4); hAAT(P), human α1-antitrypsin promoter (418 bp) (SEQ ID NO: 5); hFIX, human Factor IX cDNA (1.4 kb) (SEQ ID NO: 2); IntA, truncated human Factor IX first intron (SEQ ID NO: 1); bpA, bovine growth hormone polyadenylation signal (SEQ ID NO: 6).

Plasmid Preparations. The construction of plasmids pBS-ApoEHCR-hAATp-hFIX+IntA-bpA and pBS-hAATp-hFIX-bpA is described in Example 1, and the structure of the plasmids is shown in FIG. 7A. Large scale preparation of the plasmids was done using Qiagen maxi-prep kit (Valencia, Calif.). No protein or RNA was detected after purification.

Animal experiments. Animals were treated according to the National Institutes of Health guidelines for animal care and the guidelines of the University of Washington. Adult C57/B16 mice were purchased from Taconic (Germantown, N.Y.) and housed under SPF conditions at Virginia Mason Research Center. All methods of plasmid DNA infusion and DNA isolation are described in Example 1. Briefly, fifty micrograms of the respective plasmid in 2 ml phosphate buffered saline were injected into the tail vein of 20-24 g mice over 6-8 seconds (s). Scheduled blood samples were taken from the retro-orbital plexus. For mice undergoing partial hepatectomy, two thirds of the livers were sectioned during surgery.

DNA analyses. Genomic DNA was prepared from different tissues, including brain, heart, lung, liver, spleen, kidney, and testes from plasmid-treated mice sacrificed at different time points, and from the liver of a control mouse. Fifteen µg of sample from each preparation were digested with PstI, which has two recognition sites in the vector, at 37° C. overnight and then electrophoreses through a 0.8% agarose gel and transferred to a nylon membrane (Hybond N+; Amersham, Piscataway, N.J.). The membrane was prehybridized and then hybridized with a hFIX cDNA probe at 65° C. using a Rapid-Hyb buffer (Amersham). The final stringency of washing was 0.1×SSC-0.1% sodium dodecyl sulfate at 65° C. The probe was an 810 bp hFIX cDNA fragment spanning from exon II to exon VIII, which was labeled to a specific activity of $10^8$ cpm/µg with [$\alpha$-$^{32}$P] dCTP using a random primer labeling kit (Life Technologies, Rockville, Md.). The liver DNA samples were also left undigested, or digested with ClaI, and analyzed by Southern blot. Genomic DNA from untreated mouse liver was used as a negative control. Hirt procedure (*J. Mol. Biol.*, 26:365 (1967)) was used to isolate extrachromosomal fractions from cellular DNA. Plasmid genomes per diploid genomic DNA were calculated using the mouse metallothionein-I probe as a DNA loading standard (Snyder, R. O. et al, *Nat. Genet.*, 16:270 (1997)).

RNA analyses. The mRNA was isolated from different organs including brain, heart, lung, liver, spleen, kidney, and testis, at different time points, from sacrificed mice treated with plasmid DNA using FastTrack Kit (Invitrogen, San Diego, Calif.). The transcript was first subjected to reverse transcription using an oligo-dT primer and reverse transcriptase (Life Technologies) to generate first-strand cDNA. The resulting cDNA pool was amplified by PCR using primers spanning an 810 bp region of hFIX cDNA, (5'-GATGGAGATCAGTGTGAGTCCAATCCATGT-3' (SEQ ID NO: 17), and 5'-AGCCACTTACATAGCC AGATC-CAAATTTGA-3' (SEQ ID NO: 18)). PCR conditions were 95° C. for 1 min, 60° C. for 45 sec, and 70° C. for 1 min for 30 cycles. Control RT-PCR reactions were carried out in parallel reactions using mouse β-actin primers (Clontech, Palo Alto, Calif.).

Liver toxicity assays. To evaluate liver toxicity in mice that received plasmids or saline, blood was collected at different time points via retro-orbital bleeding into one-tenth volume of 0.15 M sodium citrate. Samples were analyzed for the presence of alanine aminotransferase (ALT), aspartate aminotransferase (AST), and total bilirubin by enzyme assay kits (Sigma, St. Louis, Mo.). Histological examination was performed on formalin-fixed mouse liver sections prepared by routine histological staining (Hematoxylin/Eosin) procedures.

Assays for Human FIX antigen and Anti-hFIX antibodies. The human Factor IX level in the mouse plasma was determined as total hFIX antigen by an ELISA using polyclonal antisera to hFIX (Snyder, R. O. et al., *Nature Genetics*, 16:270 (1997); Miao, C. H. et al., *J. Virology*, 74:3793 (2000)). Antibodies against hFIX were detected by antigen-specific ELISA. The microtiter plates were first coated with plasma-derived hFIX protein (1 mg/ml mononine, Armour Pharmaceutical, Collegeville, Pa.). Plasma taken at different time points after infusion from plasmid treated mice were diluted and applied to the coated plate. The antibodies were detected with horseradish peroxidase-conjugated antibodies (1:2000 dilution) for total murine IgG, followed by incubating with o-phenylenediamine dihydrochloride substrate. Standard curve used to determine the anti-hFIX titers was obtained by using serially diluted purified total murine IgG proteins.

EXAMPLE 4

This example describes the expression of Factor IX obtained by introducing the plasmids described in Example 3 into mouse liver cells.

Figure 7B:
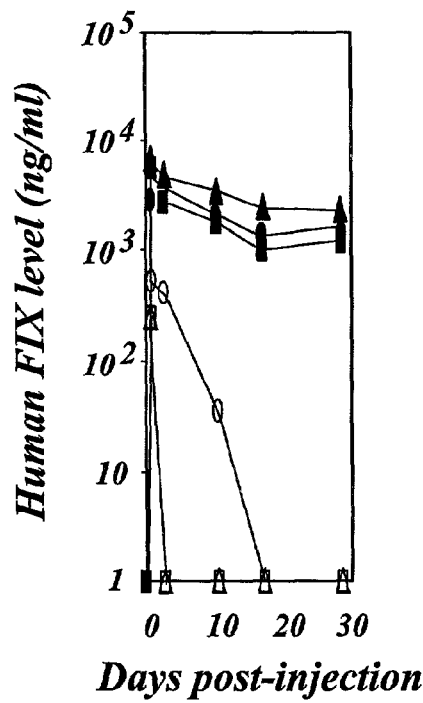
FIG. 7B shows the expression levels of hFIX over a 30 day period following naked DNA transfer into mouse livers of the two plasmids shown in FIG. 7A. Mice were rapidly (5-8 secs) infused with 20 μg of plasmid in 2 ml saline into the tail vein. Groups of mice (n=3/group) treated with each plasmid were sacrificed at 1 day (data not shown), 3 days (data not shown) and 30 days post-injection. Filled Symbols, pBS-ApoEHCR-hAATp-hFIX+IntA-bpA; open symbols, pBS-hAATp-hFIX-bpA.
Figure 7C:
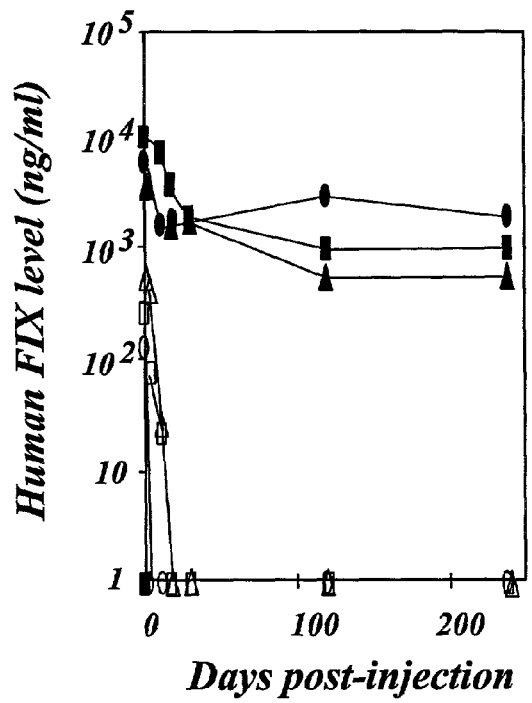
FIG. 7C shows the expression levels of hFIX over a 240 day period following naked DNA transfer into mouse livers of the two plasmids shown in FIG. 7A. Mice were rapidly (5-8 secs) infused with 20 μg of plasmid in 2 ml saline into the tail vein. Groups of mice (n=3/group) treated with each plasmid were sacrificed at 240 days post-injection. Filled Symbols, pBS-ApoEHCR-hAATp-hFIX+IntA-bpA; open symbols, pBS-hAATp-hFIX-bpA.
Figure 7D:
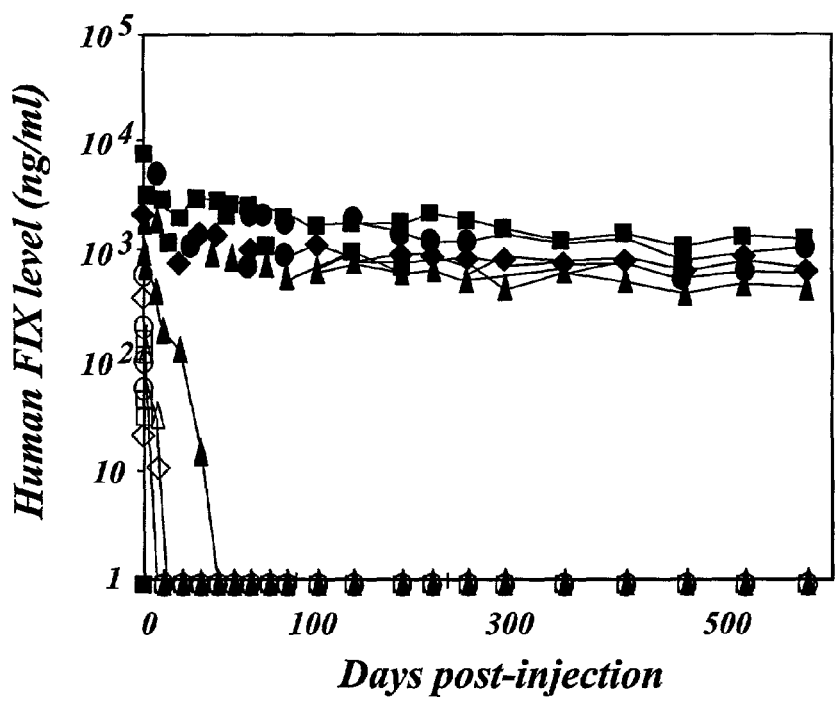
FIG. 7D shows the expression levels of hFIX over a 550 day period following naked DNA transfer into mouse livers of the two plasmids shown in FIG. 7A. Mice were rapidly (5-8 secs) infused with 20 μg of plasmid in 2 ml saline into the tail vein. Groups of mice (n=3/group) treated with each plasmid were followed for the duration of the experiment (550 days post-injection). Filled Symbols, pBS-ApoEHCR-hAATp-hFIX+IntA-bpA; open symbols, pBS-hAATp-hFIX-bpA.

Human FIX gene expression after direct plasmid injection into mouse livers. In order to explore long-term gene expression of hFIX by nonviral delivery of plasmid DNA, a series of analyses were performed at different time points with mice infused with a high expressing plasmid (pBS-ApoE-HCR-hAATp-hFIX+IntA-bpA, FIG. 7A), and a low expressing plasmid (pBS-hAATp-hFIX-bpA, FIG. 7A), respectively. The expression cassette in pBS-ApoEHCR-hAATp-hFIX+IntA-bpA contains a hepatic locus control region (HCR) (SEQ ID NO: 4), human alphal antitrypsin (hAAT) promoter (SEQ ID NO: 5), hFIX cDNA (SEQ ID NO: 2), a truncated hFIX intron A (SEQ ID NO: 1), and a bovine growth hormone polyadenylation signal (bpA) (SEQ ID NO: 6). The expression cassette in pBS-hAATp-hFIX-bpA contains a hAAT promoter (SEQ ID NO: 5), hFIX cDNA (SEQ ID NO: 2), and bpA (SEQ ID NO: 6). Twenty g of the respective plasmid was rapidly injected into the tail vein of several groups of mice. As shown in FIGS. 7B-7D, mice infused with pBS-hAATp-hFIX-bpA always produced transient, low-level Factor IX gene expression, whereas mice infused with PBS-ApoEHCR-hAATp-hFIX+IntA-bpA produced initially high-level Factor IX gene expression, averaged to 10 µg/ml of hFIX protein (normal=5 µg/ml), which decreased and stabilized at 0.5-2 µg/ml up to 550 days (duration of the experiments).

Southern analysis to examine plasmid DNA distribution in different organs over time. As a first step to examine the correlation of vector DNA and gene expression levels, we investigated the vector status in the cells. Southern analyses were performed on genomic DNA isolated from different organs, including brain, heart, lung, liver, spleen, kidney, and testes, in mice infused with plasmids and sacrificed at different time points. Consistent with other reports (Liu, F. et al., Gene Ther., 6:1258 (1999)), it was found that the majority of the DNA was taken up by the liver. Very low levels of vector DNA were observed in lung, spleen, and heart, but none was detectable in brain, kidney, and testes. This is probably because rapid delivery of the large volume of plasmid solution resulted in volume overload and back-flow into the liver associated with high-pressure delivery. Some of the plasmid solution probably distributed to other tissues and organs. For either plasmid, the amount of vector DNA retained in the cells peaked at one day, then declined and stabilized at the plateau level from 30 up to 240 days. However, there were three to four fold more vectors retained in the mouse livers injected with pBS-ApoEHCR-hAATp-hFIX+IntA-bpA compared with mice injected with pBS-hAATp-hFIX-bpA.

RT-PCR analysis of the transcripts in different tissues. RT-PCR was performed to examine the status of the transcripts in different tissues over time. Transcripts were only observed in the liver, which is as predicted from the tissue-specific promoter incorporated in the expression cassette. For high expressing plasmid pBS-ApoEHCR-hAATp-hFIX+IntA-bpA, the amount of transcript was highest one day post injection, and decreased gradually to a steady-state level over time. For low expressing plasmid pBS-hAATp-hFIX-bpA, a low level of transcript was observed one day after plasmid injection, and no transcript can be detected afterwards. Relative levels of mRNA were positively associated with protein expression levels over time. This suggested that although retention of the plasmids in the nucleus is necessary for stable expression of the transgene, the expression level was further controlled by transcriptional activation and processing to the stable transcript.

Bio-distribution of vector DNA and transcripts after slower plasmid infusion. When the high expressing hFIX plasmids pBS-ApoEHCR-hAATp-hFIX+IntA-bpA was administered into the tail vein by a less rapid injection (30 s versus 8 s), lower hFIX gene expression (80% reduction) was observed. When plasmid pBS-ApoEHCR-hAATp-hFIX+IntA-bpA was injected into the tail vein of mice at a slower rate, more vector genomes distributed into other organs instead of predominantly into liver. This is probably due to the lower pressure exerted by the injection, therefore the plasmid solution had time to flow into other tissues. However, transgene expression was only observed in the liver by RT-PCR analyses of the transcripts in different tissues. There may be trace levels of gene expression from other tissues undetectable in our experiments. This is as anticipated since the expression cassette contains liver-specific promoter (SEQ ID NO: 5) and hepatic locus control region (SEQ ID NO: 4). Restricting FIX gene expression to target liver cells limits synthesis of FIX in other tissues, lessening the induction of immune response (Pastore, L. et al., Hum. Gene Ther., 10:1773 (1999)). Restricting the expression of foreign genes in a retroviral vector to skeletal muscle cells that are inefficient at antigen presentation has also been shown to prolong the expression of a foreign gene product in mice (Pinto, V. B. et al., J. Virol., 74:10202 (2000)).

Temporal restriction analyses of vector DNA status in the liver. To determine whether the serum hFIX levels over time correlated with the amount of DNA retained in the liver cells, total cellular DNA isolated from the livers in plasmid-treated mice sacrificed at different time points were subjected to restriction analyses. A Southern blot of undigested cellular DNA extracted from mouse livers one day after gene transfer revealed the same episomal vector genomes (6.1 kb & 4.2 kb bands from pBS-ApoEHCR-hAATp-hFIX+IntA-bpA-treated mouse; 4.5 kb from pBS-hAATp-hFIX-bpA treated-mouse) as the undigested plasmid control. Additional larger size DNA bands were also observed (>12 kb from pBS-ApoEHCR-hAATp-hFIX+IntA-bpA-, and pBS-hAATp-hFIX-bpA-treated mouse, respectively), possibly due to polymerization or aggregation of plasmid DNA. All of these vector genomes gradually decreased to a steady-state level at 30 days post-infusion. Digestion of these samples with PstI released an internal fragment of 3.1 kb including hFIX cDNA (SEQ ID NO: 2) and its first intron (SEQ ID NO: 1) from pBS-ApoEHCR-hAATp-hFIX+IntA-bpA-treated mouse, and 1.7 kb containing hFIX cDNA (SEQ ID NO: 2) from pBS-hAATp-hFIX-bpA-treated mouse. When the samples were digested with ClaI that cleaves a single site in the vector, a major fragment of 6.8 kb was observed from pBS-ApoEHCR-hAATp-hFIX+IntA-bpA-treated mouse, and 4.6 kb from pBS-hAATp-hFIX-bpA-treated mouse, with the same size as the digested episomal plasmid controls. A non-specific high molecular weight band was present in the plasmid-treated mouse samples as in the naive mouse sample. The average copy numbers of vectors calculated from groups of mice were comparable between the digested and undigested samples, suggesting that most of the input vectors remained episomal.

In order to more quantitatively determine the relative abundance of integrated and episomal forms of vector DNA in the mouse liver, total liver DNA from mice 240 days post-injection was isolated using a Hirt procedure to separate the chromosomal and extra-chromosomal DNA. The DNA was extracted twice with Phenol/CHCl$_3$ before Southern analysis to remove any residual proteins. All the vector DNA were detected in the Hirt fraction, and not in the chromosomal fraction. In a control experiment, added external plasmid DNA, pBS-ApoEHCR-hAATp-hFIX+IntA-bpA, was only detected in the Hirt fraction, and not in the chromosomal fraction. These data clearly indicated that the majority of the vector DNA retained in the liver cells long-term stayed in the episomal forms.

Plasmid maintenance after partial hepatectomy of mice with persistent hFIX gene expression. Partial hepatectomy was performed in two mice 300 days after injecting plasmid pBS-ApoEHCR-hAATp-hFIX+IntA-bpA. The hFIX levels were stable at 0.9 and 0.5 µg/ml in these two mice before surgery, respectively. After partial hepatectomy, hFIX level increased transiently to higher levels (data not shown) presumably because of the induction of protein synthesis during liver regeneration process. The level then dropped to much lower levels from 7 days to 30 days after surgery, then stabilized. The mice were then sacrificed and their liver regeneration was confirmed. Based on the finding that after partial hepatectomy, liver regeneration occurs mainly from pre-existing hepatocytes, not from facultative hepatic stem cells (Braun, K. M., and Sandgren, E. P., Am. J. Pathol., 157:561 (2000); Bustos, M. et al., Am. J. Pathol., 157:549 (2000)), it was anticipated that, if the plasmids were mostly integrated after 1 month, when livers were completely regenerated (Fausto, N., J. Hepatol., 32:19 (2000)), hFIX would come back to levels similar to those observed before surgery. Since the observed level was much reduced, it suggested that transgene expression came mostly from episomal forms. It is also not surprising that the level did not come back to one third of normal due to significant loss of the plasmids during multiple rounds of cell divisions.

Liver function and toxicity test. The toxicity in the mouse livers caused by the injection procedure was examined. ALT, AST, and total bilirubin levels were determined with sera from mice injected rapidly with pBS-ApoEHCR-hAATp-hFIX+IntA-bpA, or with isotonic saline. ALT and AST levels were elevated 10-20 fold above the normal level the first day after injection, then rapidly declined to normal levels 3 and 10 days after injection (Table 2).

TABLE 2

LIVER TOXICITY AFTER DIRECT PLASMID INJECTION.

|  | Day 1 | Day 3 | Day 10 | Day 180 |
|---|---|---|---|---|
| ALT level (U/L) |  |  |  |  |
| Normal | 29 ± 7 | — | — | — |
| Saline-treated | 809 ± 459 | 89 ± 38 | 28 ± 8 | 27 ± 1 |
| Plasmid-treated | 1447 ± 829 | 44 ± 21 | 35 ± 6 | 27 ± 5 |
| AST level (U/L) |  |  |  |  |
| Normal | 36 ± 3 | — | — | — |
| Saline-treated | 395 ± 203 | 93 ± 54 | 34 ± 5 | 30 ± 2 |
| Plasmid-treated | 736 ± 424 | 44 ± 21 | 35 ± 6 | 27 ± 5 |
| Bilirubin level (mg/dL) |  |  |  |  |
| Normal | 0.15 ± 0.02 | — | — | — |
| Saline-treated | 0.32 ± 0.15 | 0.45 ± 0.39 | 0.16 ± 0.01 | 0.10 ± 0.01 |
| Plasmid-treated | 0.12 ± 0.07 | 0.22 ± 0.13 | 0.12 ± 0.02 | 0.14 ± 0.05 |

Data represent means (±standard deviation) of six mice per group. Mice were untreated (normal), or treated with either saline or plasmid pBS-ApoEHCR-hAATp-hFIX+IntA-bpA. ALT, alanine amino transferase; AST, aspartate amino transferase.

When mouse sera were tested 240 days after injection, normal ALT and AST levels were detected for all the mice (n=6 per group) examined. Serum bilirubin levels remained normal in mice treated with either plasmid or saline for all the samples. These data indicated that toxicity was acute and transient. Furthermore, it was related to rapid injection of a large volume, since the levels elevated were comparable in saline and plasmid injected animals. The liver recovered rapidly as shown by the fall in ALT and AST levels.

To further determine the extent of hepatic injury following the intravenous bolus of saline or plasmid rich fluid, separate series of treated mice (n=1 per group) were sacrificed and the livers were examined for tissue damage. For these studies, mice were given the standard tail vein bolus with saline or plasmid DNA and then sacrificed 1, 3, 10 and 180 days post-injection. The amount and pattern of tissue damage at different times correlated with the transaminase levels, found in the different series of mice (above). Gross inspection of the livers at 1 and 3 days post injection showed hepatic and splenic enlargement with focal areas of hemorrhage located primarily in a hepatic pericapsilar distribution. The total extent of damage represented less than 5% of the liver. Histologic sections showed a similar pattern with focal coagulative necrosis and hemorrhage confined primarily to the subcapsular region. Again the extent of damage represented less than 5% of the total liver with the majority of the hepatic parenchyma showing no significant histologic abnormality. No splenic lesions were detected by histologic examination. The extent of tissue damage was slightly greater in the livers from the saline control mice. However, this difference may be a result of sampling since the lesions are focal and limited in size. The fact that the saline control mice had at least as much tissue damage suggested that the damage was primarily caused by the fluid bolus and not related to the foreign plasmid DNA. Hepatic section taken from the mice 10 days post injection showed considerable reparative changes with only a mild mononuclear inflammatory infiltrate, focal collections of spindle to epithelial basophilic cells (fibroblasts and Otto cells) with several mitotic figures, and bile ductule proliferation. These focal lesions had resolved afterwards since no significant histologic abnormalities were detected in liver sections from mice 180 days post injection. There was no significant fibrosis or inflammatory infiltrate in these long-term mice indicating complete recovery from the transient hepatic damage.

Antibody formation. After gene transfer, antibody formation against either vector or transgene can cause much lower, or no protein expression even if transduction of the target cells is successful. Therefore antibodies against vector or hFIX were examined over time. No anti-plasmid antibody was observed (data not shown). Nevertheless, only very low level (3-11 µg/ml) of anti-hFIX antibodies were detected by ELISA using recombinant hFIX and a polyclonal antibody against hFIX. These very low level antibodies were detected around 10 days, peaked during 20-40 days, and declined to undetectable levels ~60 days after injection. The transient antibody formation did not prevent hFIX protein circulating in the treated mouse plasma.

Most plasmid DNA remained episomal in the liver for the duration of persistent gene expression. Episomal persistence of DNA has been used by viruses to establish latent state in the host cells. One good example is Herpes Simplex Viruses (HSV), which can persist lifelong in neurons in the latent state with absence of viral protein expression. The virus contains a unique, neuron-specific promoter system that remains transcriptionally active during latency and can be used to express therapeutic proteins without compromising the latent state (Goins, W. F. et al., *J. Virol.*, 68:2239 (1994)). It is unclear which region in the HSV promoter enables the promoter to remain active lifelong. However, it is interesting to note that the accumulated transcripts in the nuclei from latent gene expression of HSV are stable introns. Southern analyses of the DNA genome from the naked DNA transfer experiments indicated that episomal forms of the vectors are the major forms persistent in the liver. After initial fall of hFIX expression and the number of vector genomes in the cell, the amount of plasmid pBS-ApoEHCR-hAATp-hFIX+IntA-bpA was about three to four fold higher than pBS-hAATp-hFIX-bpA. However, the initial and subsequent expression levels obtained from pBS-ApoEHCR-hAATp-hFIX+IntA-bpA were 2 logs or more higher than those from pBS-hAATp-hFIX-bpA (FIG. 7). It was also observed that for plasmids containing other low-expressing cassettes, comparable amounts of the plasmid DNA as pBS-hAATp-hFIX-bpA can persist in the liver for a long time without detectable circulating transgene product.

The high-expressing vector DNA persisted at approximately 2.3 copies per diploid genome. Taking into account that 20% of the liver cells were transduced when a bluescript plasmid encoding β-galactosidase gene was injected rapidly through the tail vein of mice. Each transduced liver cell contained approximately 11 copies of the plasmid. It has been shown that when a plasmid first enters the nucleus, the DNA is immediately condensed into nucleosome-like structure by histones and other molecules (Cereghini, S., and Yaniv, M., *EMBO J.*, 3:1243 (1984); Jeong, S., and Stein, A., *Nuc. Acids. Res.*, 22:370 (1994)). The rapid decline in the amount of DNA and transgene expression in the first few days may be due to a combination of elimination of transduced cells damaged in the infusion process and degradation of any unstable plasmid DNA in the nucleus. The remaining plasmids probably persist in the nucleosome-like structure and are associated with one or more specific nuclear compartments. However, only plasmids with certain regulatory DNA sequences were able to produce prolonged high-level gene expression. It is possible that the established high-expressing hFIX cassettes meet the requirement for episomal persistence of plasmids and preservation of active promoters. Hepatic locus control region (HCR) (SEQ ID NO: 4) from the ApoE gene locus (Simonet, W. S. et al., *J. Biol. Chem.*, 268:8221 (1993)) contains DNase I hypersensitive sites, and is primarily responsible for keeping the chromatin transcriptionally active. Furthermore, the ApoE-HCR (SEQ ID NO: 4) contains a matrix attachment region (MAR) as well as liver-specific enhancer elements, which may augment gene expression in the plasmid (Dang, Q. et al., *J. Biol. Chem.*, 270:22577 (1995)). The MAR and intronic sequences together may interact with the nuclear matrix (Gindullis, F., and Meier, I., *Plant Cell*, 11:1117 (1999); Meissner, M. et al., *J. Cell. Biochem.*, 76:559 (2000); Wei, X. et al., *J. Cell. Biol.*, 146:543 (1999)), and may be primarily responsible for the persistence of gene expression from the plasmid DNA.

An alternative possibility is that some of the vector genomes have integrated into the cellular chromosome, and contributed to long-term gene expression. Although this cannot be ruled out at this time, the results reported herein argue against significant genomic integration. First, liver regeneration after partial hepatectomy resulted in a substantial decline in hFIX level, suggesting regeneration and cell replication were detrimental to plasmid maintenance. Second, Southern blot analyses showed that the average copy numbers of low molecular weight vectors calculated from groups of mice were comparable between the digested and undigested samples, and most of the vector DNA had restriction digest fragments identical to those seen in the plasmid control. These results agree with those obtained by Wolff (Wolff, J. A. et al., *Hum. Mol. Genet.*, 1:363 (1992)) and others (Monthorpe, M. et al., *Hum. Gene Ther.*, 4:419 (1993)) who did not identify any integration events of plasmid DNAs in muscle cells after naked DNA transfer.

Nonviral gene transfer of 1 plasmid DNA into liver produced neither long-term immune response nor toxicity. Gene transfer by viral vectors usually elicits immune responses against transgene and/or vectors. Adenoviral gene transfer can activate strong hFIX-specific cytotoxic T lymphocyte and B-cell responses, leading to the destruction of transduced cells and elimination of transgene expression. On the other hand, AAV-mediated gene transfer of hFIX-induced T and B cell responses that are more comparable to responses in the setting of protein infusion rather than of viral infection/gene transfer in muscle cells (Fields, P. A. et al., *Mol. Ther.*, 1:225 (2000)). It has also been reported that in muscle cells, non-viral plasmid-mediated gene transfer resulted in infiltrates of neutrophils and other inflammatory cells and some loss of structural integrity of muscle tissue, leading to undetectable levels of hFIX expression. The inflammation of injected muscle with mononuclear infiltrate comprised largely macrophages and both CD4+ and CD8+T lymphocytes (McMahon, J. M. et al., *Gene Ther.*, 5:1283 (1998)). These were attributed to hypomethylation of plasmids, which were prepared from bacterial culture.

In this study, initial hepatic injury was expected due to high hydrostatic pressure exerted by the rapid infusion of a large volume into the mice. Nevertheless, histological examination at days 1 and 3 showed that >95% of the liver appeared normal. Mild mixed inflammatory infiltrate with reparative changes was established rapidly so that the majority of the tissue damage was repaired within 10 days post-infusion. In all sections examined, there was somewhat less tissue damage in the livers treated with plasmid than the saline control. These results indicated that transient inflammation was caused by the injection procedure non-specifically rather than by the plasmid DNA or transgene expression.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A nucleic acid expression cassette capable of expressing human Factor IX, wherein the cassette is predominantly expressed in the mammalian liver, said cassette comprising:
   (a) a hepatic locus control element consisting of SEQ ID NO:4 or SEQ ID NO:9;
   (b) a heterologous hepatic promoter located 3' to the hepatic locus control element, said promoter consisting of SEQ ID NO: 5;
   (c) a Factor IX coding sequence located 3' to the hepatic promoter, said coding sequence comprising SEQ ID NO:2;
   (d) a polyadenylation signal located 3' to the intron sequence, said polyadenylation signal consisting of SEQ ID NO:6; and
   (e) an intron located 3' to the hepatic promoter and 5' to the polyadenylation signal, wherein said intron consists of SEQ ID NO:1,
   wherein elements (a), (b), (c), (d) and (e) are operably linked to express the polypeptide encoded by the coding sequence.

2. The expression cassette of claim 1, wherein said cassette directs expression of a therapeutic amount of Factor IX in liver cells for a period of at least 100 days, and further wherein said cassette is expressed in an animal or as a component of a recombinant adeno-associated virus (AAV) vector.

3. The expression cassette of claim 1, wherein said cassette directs expression of a therapeutic amount of the polypeptide in liver cells for a period of at least 300 days, and further wherein said cassette is expressed in an animal or as a component of a recombinant adeno-associated virus (AAV) vector.

4. The expression cassette of claim 1, wherein said cassette directs expression of a therapeutic amount of the polypeptide in liver cells for a period of at least 500 days, and further wherein said cassette is expressed in an animal or as a component of a recombinant adeno-associated virus (AAV) vector.

5. A nucleic acid expression cassette capable of expressing human Factor IX, wherein the cassette is predominantly expressed in the mammalian liver, said cassette comprising:
   (a) a hepatic locus control element consisting of SEQ ID NO:4 or SEQ ID NO:9;
   (b) a hepatic promoter located 3' to the hepatic locus control element, said promoter consisting of SEQ ID NO:5;
   (c) a Factor IX coding sequence located 3' to the hepatic promoter, said coding sequence comprising SEQ ID NO:2;
   (d) a polyadenylation signal located 3' to the intron sequence, said polyadenylation signal consisting of SEQ ID NO:6; and
   (e) an intron located 3' to the hepatic promoter and 5' to the polyadenylation signal, wherein said intron consists of SEQ ID NO:1, and
   (f) an untranslated region located 3' to the coding region and the intron, said untranslated region consisting of SEQ ID NO:7;
   wherein elements (a), (b), (c), (d) and (e) are operably linked to express the polypeptide encoded by the coding sequence.

6. The expression cassette of claim 5, wherein said cassette directs expression of a therapeutic amount of Factor IX in liver cells for a period of at least 100 days, and further wherein said cassette is expressed in an animal or as a component of a recombinant adeno-associated virus (AAV) vector.

7. The expression cassette of claim 5, wherein said cassette directs expression of a therapeutic amount of the polypeptide in liver cells for a period of at least 300 days, and further wherein said cassette is expressed in an animal or as a component of a recombinant adeno-associated virus (AAV) vector.

8. The expression cassette of claim 5, wherein said cassette directs expression of a therapeutic amount of the polypeptide in liver cells for a period of at least 500 days, and further wherein said cassette is expressed in an animal or as a component of a recombinant adeno-associated virus (AAV) vector.

* * * * *

UNITED STATES PATENT AND TRADEMARK OFFICE
CERTIFICATE OF CORRECTION

| | | |
|---|---|---|
| PATENT NO. | : 7,351,813 B2 | Page 1 of 1 |
| APPLICATION NO. | : 09/884901 | |
| DATED | : April 1, 2008 | |
| INVENTOR(S) | : Miao et al. | |

It is certified that error appears in the above-identified patent and that said Letters Patent is hereby corrected as shown below:

In The Specification Under Column 1:

• Please replace lines 12-15 with:

--This invention was made with Government support under contract DKD49022 awarded by the National Institutes of Health. The Government has certain rights in this invention.--

Signed and Sealed this

Nineteenth Day of April, 2011

David J. Kappos
*Director of the United States Patent and Trademark Office*